United States Patent
Souza et al.

(10) Patent No.: US 9,695,187 B2
(45) Date of Patent: Jul. 4, 2017

(54) SYNTHETIC PROCESS FOR PREPARATION OF MACROCYCLIC C1-KETO ANALOGS OF HALICHONDRIN B AND INTERMEDIATES USEFUL THEREIN

(71) Applicant: ALPHORA RESEARCH INC., Mississauga (CA)

(72) Inventors: Fabio E. S. Souza, Mississauga (CA); Alena Rudolph, Puslinch (CA); Ming Pan, Mississauga (CA); Boris Gorin, Oakville (CA); Teng Ko Ngooi, Mississauga (CA); Jason A. Bexrud, Toronto (CA); Ricardo Orprecio, Etobicoke (CA); Huzaifa Rangwala, Mississauga (CA)

(73) Assignee: ALPHORA RESEARCH INC., Mississauga, Ontario (CA)

( * ) Notice: Subject to any disclaimer, the term of this patent is extended or adjusted under 35 U.S.C. 154(b) by 0 days.

(21) Appl. No.: 15/015,161

(22) Filed: Feb. 4, 2016

(65) Prior Publication Data

US 2016/0152631 A1  Jun. 2, 2016

Related U.S. Application Data

(62) Division of application No. 14/389,439, filed as application No. PCT/CA2013/050254 on Mar. 28, 2013, now Pat. No. 9,278,979.

(60) Provisional application No. 61/618,004, filed on Mar. 30, 2012, provisional application No. 61/647,127, filed on May 15, 2012.

(51) Int. Cl.
| | |
|---|---|
| *C07D 493/22* | (2006.01) |
| *C07D 407/14* | (2006.01) |
| *C07D 493/04* | (2006.01) |
| *C07D 307/20* | (2006.01) |
| *C07C 309/04* | (2006.01) |

(52) U.S. Cl.
CPC .......... *C07D 493/22* (2013.01); *C07C 309/04* (2013.01); *C07D 307/20* (2013.01); *C07D 407/14* (2013.01); *C07D 493/04* (2013.01)

(58) Field of Classification Search
CPC .................................................. C07D 493/22
USPC ......................................................... 549/396
See application file for complete search history.

(56) References Cited

U.S. PATENT DOCUMENTS

| | | | |
|---|---|---|---|
| 5,436,238 | A | 7/1995 | Kishi et al. |
| 6,214,865 | B1 | 4/2001 | Littlefield et al. |
| 2004/0192885 | A1 | 9/2004 | Sharma et al. |

FOREIGN PATENT DOCUMENTS

| | | |
|---|---|---|
| CA | 2166898 | 9/2004 |
| WO | 93/17690 | 9/1993 |
| WO | 99/65894 | 12/1999 |
| WO | 2005118565 | 12/2005 |
| WO | 2009/124237 | 10/2009 |
| WO | 2013/078559 | 6/2013 |
| WO | 2013/086634 | 6/2013 |
| WO | 2013/097042 | 7/2013 |
| WO | 2014/183211 | 11/2014 |

OTHER PUBLICATIONS

Narayan et al., Bioorg. Med. Chem. Letters, (2011), vol. 21, pp. 1630-1633.*
Choi et al., "Synthetic studies on the marine natural product halichondrins", Pure Appl. Chem., vol. 75, No. 1, pp. 1-17, 2003, Massachusetts (CHOI_ET_AL_1).
Choi et al., "Asymmetric Ni(II)/Cr(11)-Mediated Coupling Reaction: Catalytic Process", Organic Letters, vol. 4, No. 25, pp. 4435-4438, 2002, Massachusetts (CHOI_ET_AL_2).
Cook et al., "Total Synthesis of (--)-Exiguolide", Organic Letters, vol. 12, No. 4, pp. 744-747, 2010, France.
Dong et al., "New Syntheses of E7389 C14-C35 and Halichondrin C14-C38 Building Blocks: Reductive Cyclization and Oxy-Michael Cyclization Approaches", J. Am. Chem. Soc., vol. 131, pp. 15642-15646, 2009, Massachusetts.
Guo et al., "Toolbox Approach to the Search for Effective Ligands for Catalytic Asymmetric Cr-Mediated Coupling Reactions", J. Am. Chem. Soc., vol. 131, pp. 15387-15393, 2009, Massachusetts.
Han et al., "Iridium-Catalyzed anti-Diastereo- and Enantioselective Carbonyl (Trimethylsilyl)allylation from the Alcohol of Aldehyde Oxidation Level", J. Am. Chem. Soc., vol. 132, pp. 9153-9156, 2010, Texas (HAN_ET_AL_1).

(Continued)

*Primary Examiner* — Taofiq A Solola
(74) *Attorney, Agent, or Firm* — Grossman, Tucker, Perreault & Pfleger, PLLC

(57) ABSTRACT

Disclosed is a compound of formula 1, or a pharmaceutically acceptable salt thereof, where $R^1$, $R^2$, $R^3$, $R^4$, $R^5$, $R^6$, $R^7$, $R^{7'}$, $R^8$, $R^9$, $R^{10}$, $R^{11}$, $R^{12}$ and $R^{13}$ are as disclosed herein. Also, disclosed is a process for the preparation of the compound of formula 1, or a pharmaceutically acceptable salt thereof, and intermediates used therein. The compound of formula 1 can be used in the preparation of halichondrin analogs, such as Eribulin; and a process for its preparation from the compound of formula 1 is also disclosed.

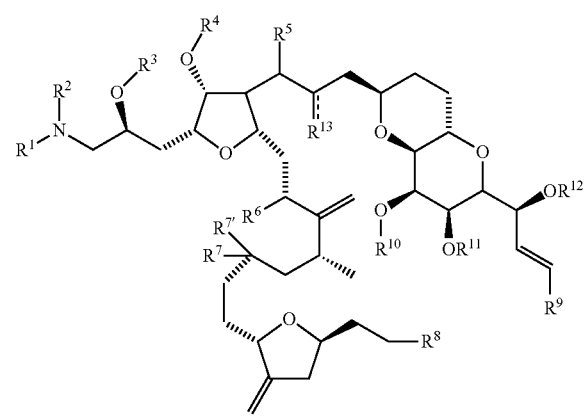

4 Claims, No Drawings

(56) References Cited

OTHER PUBLICATIONS

Han et al., Supporting Information to "Iridium-Catalyzed anti-Diastereo- and Enantioselective Carbonyl (Trimethylsilyl) allylation from the Alcohol of Aldehyde Oxidation Level", J. Am. Chem. Soc., vol. 132, pp. 9153-9156, 2010, Texas (HAN_ET_AL_2).

Jackson et al., "A Total Synthesis of Norhalichondrin B", Angewandte Chemie, vol. 48, No. 13, pp. 1-132, 2009, Colorado (JACKSON_ET_AL_1).

Jackson et al., "The Halichondrins and E7389", Chem. Rev., vol. 109, pp. 3044-3079, 2009, Colorado (JACKSON_ET_AL_2).

Jiang et al., "A Practical Synthesis of the F-Ring of Halichondrin B via Ozonolytic Desymmetrization of C2-Symmetric Dihydroxycyclohexene", J. Org. Chem., vol. 68, pp. 1150-1153, 2003, Wisconsin (JIANG_ET_AL_1).

Jiang et al., "A Novel Route to the F-Ring of Halichondrin B. Diastereoselection in Pd(0)-Mediated meso and C2 Diol Desymmetrization", Organic Letters, vol. 4, No. 20, pp. 3411-3414, 2002, Wisconsin (JIANG_ET_AL_2).

Kim et al., "New Syntheses of E7389 C14-C35 and Halichondrin C14-C38 Building Blocks: Double-Inversion Approach", J. Am. Chem. Soc., vol. 131, pp. 15636-15641, 2009, Massachusetts.

Kunznetsov et al., "Induction of Morphological and Biochemical Apoptosis following Prolonged Mitotic Blockage by Halichondrin B Macrocyclic Ketone Analog E7389", Cancer Research, vol. 64, pp. 5760-5766, 2004, Japan.

Litaudon et al., "Isohomoalichondrin B, a New Antitumour Polyether Macrolide from the New Zealand Deep-Water Sponge *Lissodendoryx* sp.", Tetrahedron Letters, vol. 35, No. 50, pp. 9435-9438, 1994, New Zealand.

Narayan et al., "Novel second generation analogs of eribulin. Part I: Compounds containing a lipophilic C32 side chain overcome P-glycoprotein susceptibility", Bioorganic & Medicinal Chemistry Letters, vol. 21, pp. 1630-1633, 2011, Massachusetts (NARAYAN_ET_AL_1).

Narayan et al., "Novel second generation analogs of eribulin. Part II: Orally available and active against resistant tumors in vivo", Bioorganic & Medicinal Chemistry Letters, vol. 21, pp. 1634-1638, 2011, Massachusetts (NARAYAN_ET_AL_2).

Narayan et al., "Novel second generation analogs of eribulin. Part III: Blood-brain barrier permeability and in vivo activity in a brain tumor model", Bioorganic & Medicinal Chemistry Letters, vol. 21, pp. 1639-1643, 2011, Massachusetts (NARAYAN_ET_AL_3).

Okouneva et al., "Inhibition of centromere dynamics by eribulin (E7389) during mitotic metaphase", Mol. Cancer Ther., vol. 7, No. 7, pp. 2003-2011, 2008, California.

Rudolph et al., "Early introduction of the amino group to the C27-C35 building block of Eribulin", Tetrahedron Letters, vol. 54, pp. 7059-7061, 2013, Canada.

Sabitha et al., "Synthesis of the C45-C53 tetrahydropyran domain of norhalichondrins and the C14-C22 tetrahydrofuran domain of the halichondrin family", RSC Advances, vol. 2, pp. 10157-10159, 2012, India.

Sartillo-Piscil et al., "Diastereoselective synthesis of 1,2-O-isopropylidene-1,6-dioxaspiro[4,4]nonane applying the methodology of generation of radical cations under non-oxidizing conditions", Tetrahedron Letters, vol. 44, pp. 3919-3921, 2003, Mexico.

Sun et al., "Synthesis and Olefination Reactions of an a-Enal from Diacetone Glucose", Communications Synthesis, pp. 28-29, 1982, Maryland.

Trost et al., "Ru-Catalyzed Alkene-Alkyne Coupling. Total Synthesis of Amphidinolide P", J. Am. Chem. Soc., vol. 127, pp. 17921-17937, 2005, California.

Wang et al., "Structure-Activity Relationships of Halichondrin B Analogues: Modifications at C.30-C.38", Bioorganic & Medicinal Chemistry Letters, vol. 10, pp. 1029-1032, 2000, Massachusetts.

Zheng et al., "Macrocyclic ketone analogues of halichondrin B", Bioorganic & Medicinal Chemistry Letters, vol. 14, pp. 5551-5554, 2004, Massachusetts.

International Search Report and Written Opinion from corresponding PCT Appln. No. PCT/CA2012/050859, dated Jan. 29, 2013.

International Search Report and Written Opinion from related PCT Appln. No. PCT/CA2012/050939, dated Feb. 15, 2013.

International Search Report and Written Opinion from related PCT Appln. No. PCT/CA2013/050254, dated Jul. 8, 2013.

International Preliminary Report on Patentability from related PCT Appln. No. PCT/CA2012/050897, dated Jun. 17, 2014.

International Preliminary Report on Patentability from related PCT Appln. No. PCT/CA2012/050939, dated Jul. 1, 2014.

International Search Report from related PCT Appln. No. PCT/CA2014/050504, dated Jul. 24, 2014.

International Search Report and Written Opinion from related PCT Appln. No. PCT/CA2014/050438, dated Jul. 25, 2014.

Office Action from related U.S. Appl. No. 14/361,489 dated Dec. 18, 2014.

* cited by examiner

SYNTHETIC PROCESS FOR PREPARATION OF MACROCYCLIC C1-KETO ANALOGS OF HALICHONDRIN B AND INTERMEDIATES USEFUL THEREIN

CROSS REFERENCE TO RELATED APPLICATIONS

This application is a divisional of U.S. patent application Ser. No. 14/389,439 filed Sep. 30, 2014, now U.S. Pat. No. 9,278,979, issued March 8, 2016, which claims the benefit of and priority to US Provisional Application Numbers 61/618,004 filed Mar. 30, 2012 and 61/647,127 filed May 15, 2012. The contents of the above applications are incorporated herein by reference.

FIELD

The specification relates to a synthetic process for preparation of macrocyclic C1-keto analogs of Halichondrin B, their salts and intermediates useful for their preparation.

BACKGROUND

Halichondrins have been disclosed as having anti-cancer and antimitotic activity (*Chem. Rev.* 2009, 109, 3044-3079, incorporated herein by reference). In particular, Halichondrin B has been reported as a potent anticancer agent that was first isolated from the marine sponge *Halichondria okadai* (U.S. Pat. No. 5,436,238; *Tetrahedron Lett.* 1994, 35, 9435 and WO 1993/017690 A1, all incorporated herein by reference). It was further reported that analogs of Halichondrin B bearing only macrocyclic fragment of its molecule (C1-C30 fragment) and having a ketone function instead of ester at C1 position demonstrate anticancer activity similar to Halichondrin B (Bioorg. Med. Chem. Lett., 2000, 10, 1029 and *Bioorg. Med. Chem. Lett.,* 2004, 14, 5551) It was established that such macrocyclic fragment is responsible for induction of mitotic blocks in cancer cells via disruption of tubulin polymerization process that triggers apoptosis of cancerous cells and stops their proliferation (Cancer Res., 2004, 64, 5760 and Mol. Canc. Ther., 2008, 7, 2003). Eribulin mesylate, a macrocyclic C1-keto analog of Halichondrin B, has been reported as having potent anticancer properties (WO 1999/065894 A1, incorporated herein by reference). Eribulin is marketed under the trade name Halaven, and it is also known as E7389, B 1939 and ER-086526.

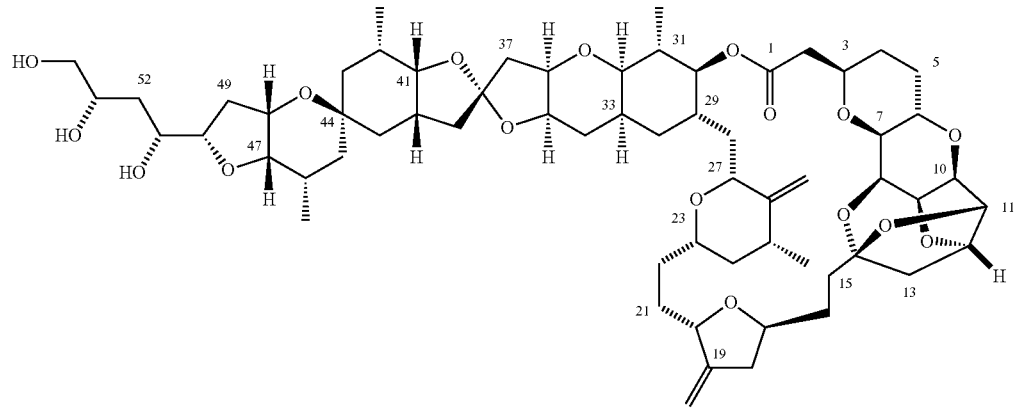

Halichondrin B

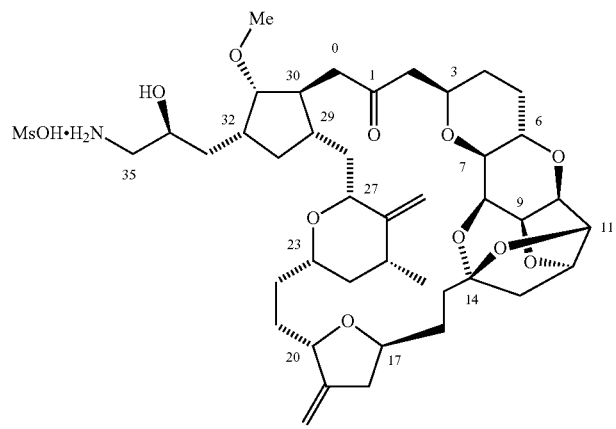

Eribulin mesylate

The synthetic approach described (U.S. Pat. No. 6,214, 865; WO 2009/124237 A1, *Bioorg. Med. Chem. Lett.*, 2004, 14, 5551 and *J. Am. Chem. Soc.* 2009, 131, 15642, all incorporated herein by reference) involves introduction of nitrogen in the C27-C35 fragment of Eribulin after assembly of the macrocycle. Such an approach can add synthetic steps to the later stages of the synthesis, after the building blocks corresponding to the C1-C13 and C14-C26 fragments have been introduced. The synthesis of those fragments is long and complex; and every additional step in the synthesis can imply an increase in manufacturing costs. In addition, due to the cytotoxic nature of Eribulin, late introduction of the nitrogen results in a greater number of steps that can require special safety containment, which can limit throughput and can also increase the cost of producing the active pharmaceutical ingredient (API).

There is a need in the art for a compound that can be used in process for preparation of Eribulin and other macrocyclic C1-keto analogs of Halichondrin B and their salts. In addition, there is a need in the art for a compound and a process that can help to improve the convergence of the synthetic route for preparation of Eribulin and other macrocyclic C1-keto analogs of Halichondrin B and their salts, and therefore, can also help to reduce the amount of C1-C13 and C14-C26 fragments required. Further, there is a need in the art for a compound that can help to reduce the number of steps that can require safety containment for preparation of Halichondrin and its analogs. Moreover, there is a need in the art for a process for preparation of such a compound.

SUMMARY OF THE INVENTION

In one aspect, the specification relates to a compound of formula 1, or a pharmaceutically acceptable salt thereof,

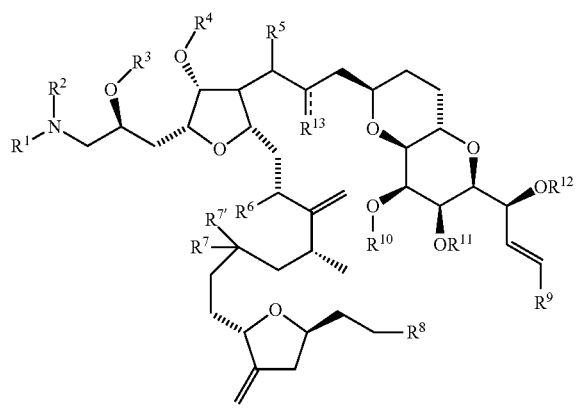

1 wherein $R^1$, $R^2$, $R^3$, $R^4$, $R^5$, $R^6$, $R^7$, $R^{7'}$, $R^8$, $R^9$, $R^{10}$, $R^{11}$, $R^{12}$ and $R^{13}$ are as described herein.

In another aspect, the specification relates to a compound of formula 2, or a pharmaceutically acceptable salt thereof,

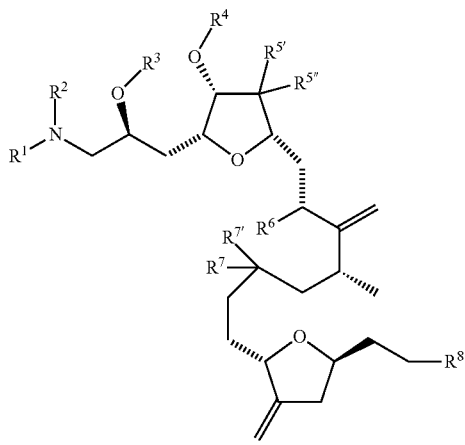

2 wherein $R^1$, $R^2$, $R^3$, $R^4$, $R^{5'}$, $R^{5''}$, $R^6$, $R^7$, $R^{7'}$ and $R^8$ are as described herein.

In a further aspect, the specification relates to a compound of formula 5, or a pharmaceutically acceptable salt thereof,

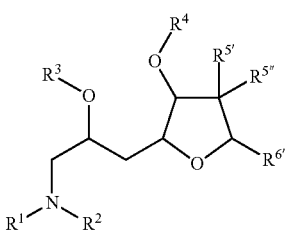

5 wherein $R^1$, $R^2$, $R^3$, $R^4$, $R^{5'}$, $R^{5''}$ and $R^{6'}$ are as described herein.

In still another aspect, the specification relates to a process for preparation of analogs of halichondrin, including eribulin, from the compound of formula 1, 2 or 5.

In a still further aspect, the specification relates to a process for preparation of the compound of formula 1, 2 or 5, or a pharmaceutically acceptable salt thereof.

DESCRIPTION

As described above, in one aspect the specification relates to a compound of formula 1, or a pharmaceutically acceptable salt thereof:

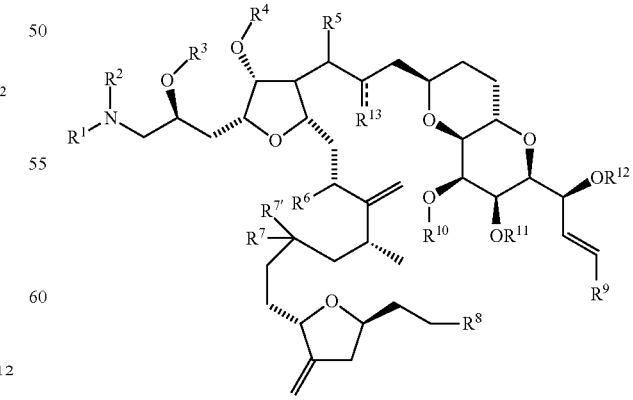

1 wherein
$R^1$ and $R^2$ each independently is H, a silyl group, an acyl group, a sulfonyl group or an alkoxycarbonyl group; or one of $R^1$ and $R^2$ is absent and the other $R^1$ or $R^2$ together with the nitrogen atom to which it is attached form an azide;

$R^3$ is H or an alcohol protecting group;

or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms;

$R^4$ is H, $C_{1-3}$ alkyl, $C_{1-3}$ haloalkyl or an alcohol protecting group;

$R^5$ is H or —$SO_2$Ar, wherein Ar is an aryl group;

$R^6$ is $OR^{16}$, wherein $R^{16}$ is H or an alcohol protecting group;

$R^7$ and $R^{7'}$ together form a =O or a protected geminal diol, or one of $R^7$ and $R^{7'}$ is H and the other is a leaving group or a functional group that can be converted into a leaving group;

or $R^6$ and one of $R^7$ and $R^{7'}$ together form —O—, and the other $R^7$ or $R^{7'}$ is H;

$R^8$ is —C(=O)$R^{17}$ or —$CH_2OR^{18}$; wherein $R^{17}$ is H or $OR^{19}$, wherein $R^{19}$ is H or a hydrocarbon, the hydrocarbon optionally having one or more heteroatoms;

$R^{18}$ is H or an alcohol protecting group;

$R^9$ is a halide or a sulfonate;

or $R^8$ and $R^9$ together form —C(=O)— or —CH($OR^{20}$)—; wherein $R^{20}$ is H or an alcohol protecting group;

$R^{10}$, $R^{11}$ and $R^{12}$ each independently is H or an alcohol protecting group;

- - - - - (representing the bond between R13 and the carbon-backbone of molecule 1) is a single or double bond; and $R^{13}$ is =O or —$PR^{21}$, wherein $R^{21}$ is H or an alcohol protecting group.

In one embodiment, the compound of formula 1 has the structure of formula 1a.

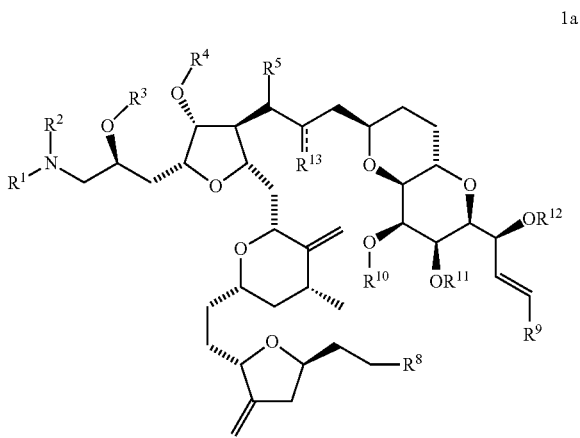

1a where $R^1$, $R^2$, $R^3$, $R^4$, $R^5$, $R^8$, $R^9$, $R^{10}$, $R^{11}$, $R^{12}$, $R^{13}$ and - - - - - are as described above.

In another aspect, the specification relates to a compound of formula 2, or a pharmaceutically acceptable salt thereof

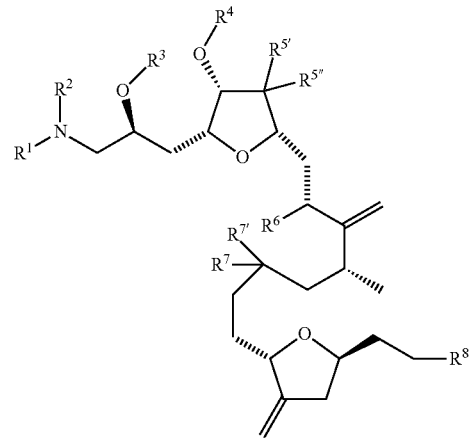

2 wherein $R^1$ and $R^2$ each independently is H, a silyl group, an acyl group, a sulfonyl group or an alkoxycarbonyl group; or one of $R^1$ and $R^2$ is absent and the other $R^1$ or $R^2$ together with the nitrogen atom to which it is attached form an azide;

$R^3$ is H or an alcohol protecting group;

or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms;

$R^4$ is H, $C_{1-3}$ alkyl or $C_{1-3}$ haloalkyl, or an alcohol protecting group;

one of $R^{5'}$ and $R^{5''}$ is H and the other is —$CH_2OR^{28}$ or —$CH_2SO_2$—Ar, or $R^{5'}$ and $R^{5''}$ taken together form =CH—$SO_2$—Ar, wherein $R^{28}$ is H or an alcohol protecting group; and Ar is an aryl group;

$R^6$ is $OR^{16}$, wherein $R^{16}$ is H or an alcohol protecting group;

$R^7$ and $R^{7'}$ together form a =O or a protected geminal diol, or one of $R^7$ and $R^{7'}$ is H and the other is a leaving group or a functional group that can be converted into a leaving group;

or $R^6$ and one of $R^7$ and $R^{7'}$ together form —O—, and the other $R^7$ or $R^{7'}$ is H;

$R^8$ is —C(=O)$R^{17}$ or —$CH_2OR^{18}$; wherein $R^{17}$ is H or $OR^{19}$, wherein $R^{19}$ is H or a hydrocarbon, the hydrocarbon optionally having one or more heteroatoms;

$R^{18}$ is H or an alcohol protecting group.

In one embodiment, the compound of formula 2 has the structure of formula 2a.

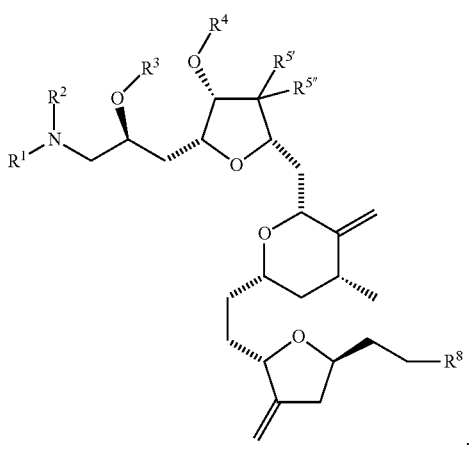

2a

In a further aspect, the specification relates to a compound of formula 5, or a pharmaceutically acceptable salt thereof,

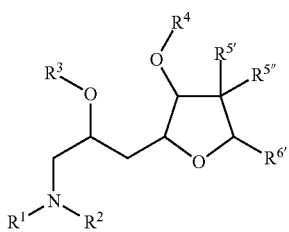

5 wherein,
- $R^1$ and $R^2$ each independently is H, a silyl group, an acyl group, a sulfonyl group or an alkoxycarbonyl group; or one of $R^1$ and $R^2$ is absent and the other $R^1$ or $R^2$ together with the nitrogen atom to which it is attached form an azide;
- $R^3$ is H or an alcohol protecting group;
- or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms;
- $R^4$ is H, $C_{1-3}$ alkyl or $C_{1-3}$ haloalkyl or an alcohol protecting group;
- one of $R^{5\prime}$ and $R^{5\prime\prime\prime}$ is H and the other —$CH_2OR^{28}$ or —$CH_2SO_2$—Ar, or $R^{5\prime}$ and $R^{5\prime\prime\prime}$ taken together form =O or =CH—$SO_2$—Ar, wherein
- $R^{28}$ is H or an alcohol protecting group; and
- Ar is an aryl group; and
- $R^{6\prime}$ is —$CH_2$—CH=$CR^{29}R^{29\prime}$, —$CH_2C$(=O)—$R^{25}$ or —$CH_2$—$CH_2$—O—$R^{26}$, wherein
- $R^{29}$ and $R^{29\prime}$ each independently is H or a hydrocarbon, the hydrocarbon optionally having one or more heteroatoms;
- $R^{25}$ is H or $OR^{27}$, wherein $R^{27}$ is H or a hydrocarbon, the hydrocarbon optionally having one or more heteroatoms;
- $R^{26}$ is H or an alcohol protecting group; or
- $R^{6\prime}$ and one of $R^{5\prime}$ and $R^{5\prime\prime\prime}$ together form a protected vicinal diol.

In one embodiment, the compound of formula 5 has the structure of formula 5a.

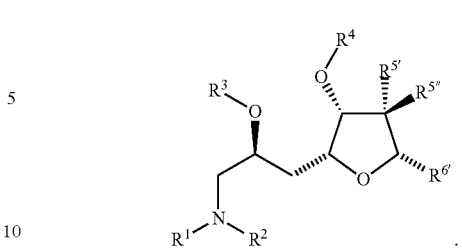

5a

The pharmaceutically acceptable salts as disclosed herein are not particularly limited and should be known to a skilled worker, or can be determined. There are no particular limitations on the pharmaceutically acceptable salt so long as eribulin or an intermediate, and salt are formed, whether inorganic acid salt or organic acid salt. For example and without limitation, the salt can be hydrochloric acid salt, sulfuric acid salt, citrate, hydrobromic acid salt, hydroiodic acid salt, nitric acid salt, bisulfate, phosphoric acid salt, isonicotinic acid salt, acetic acid salt, lactic acid salt, salicic acid salt, tartaric acid salt, pantotenic acid salt, ascorbic acid salt, succinic acid salt, maleic acid salt, fumaric acid salt, gluconic acid salt, saccharinic acid salt, formic acid salt, benzoic acid salt, glutaminic acid salt, methanesulfonic acid salt (also referred to as mesylic acid salt), ethanesulfonic acid salt, benzenesulfonic acid salt, p-toluenesulfonic acid salt, pamoic acid salt (pamoate), and so on. Preferable among these are hydrochloric acid salt, sulfuric acid salt, acetic acid salt, phosphoric acid salt, citrate, and methanesulfonic acid salt, and most preferable of all is methanesulfonic acid salt. That is, the preferable active compound of the present invention is eribulin mesylate. Eribulin or its pharmaceutically acceptable salt is the compound or its salt as recorded in PCT International Publication WO 99/65894 or U.S. Pat. No. 6,214,865 (the contents of which are incorporated herein by reference).

The term "silyl group" as used herein is not particularly limited, and should be known to a person of skill in the art. In one embodiment, for example and without limitation, the silyl group refers to the general formula "$R^3Si$—", where each R is a hydrocarbon and can be the same or different. The silyl group can include the silyl protecting groups noted herein. In a further embodiment, for example and without limitation, the silyl group can optionally have one or more heteroatoms.

The term "acyl group" as used herein is not particularly limited, and should be known to a person of skill in the art. In one embodiment, for example and without limitation, the acyl group refers to the general formula "RC(=O)—", where R is a hydrocarbon; and can also include the acyl protecting groups noted herein.

The term "sulfonyl group" as used herein is not particularly limited, and should be known to a person of skill in the art. In one embodiment, for example and without limitation, the sulfonyl group refers to the general formula "$RSO_2$—", where R is a hydrocarbon. In a further embodiment, for example and without limitation, the sulfonyl group can optionally have one or more heteroatoms.

The term "alkoxycarbonyl group" as used herein is not particularly limited, and should be known to a person of skill in the art. In one embodiment, for example and without limitation, the alkoxycarbonyl group refers to the general formula "R—O—C(=O)—", where R is a hydrocarbon.

The term "alcohol protecting group" as used herein is not particularly limited, and should be known to a skilled worker or can be determined. In one embodiment, for example and without limitation, the protecting group forms an ester, ether or is a silyl-protecting group. In a further, embodiment for example and without limitation, the ester formed is acetyl (Ac), benzoyl (Bz) or pivaloyl (Piv). In another embodiment, for example and without limitation, the ether protecting group formed is benzyl (Bn), β-methoxyethoxymethyl ether (MEM), trityl (Tr), dimethoxy trityl (DMT), methoxymethyl ether (MOM), or the like. In a still further embodiment, for example and without limitation, the silyl protecting group formed is tert-butyldimethylsilyl (TBDMS or TBS), tri-iso-propylsilyloxymethyl (TOM), or triisopropylsilyl (TIPS). In addition, the terms "protected geminal diol" and "protected vicinal diol" can have, for example and without limitation, two protecting groups for the hydroxyl groups, where the protecting groups can be as noted above. Alternatively, other diol protecting groups, such as, for example and without limitation, a ketal can also be used.

The term "hydrocarbon", as used herein, refers to a group that contains hydrogen and carbon, linked generally via a carbon backbone, but may optionally include heteroatoms. Thus, groups like methyl, ethoxyethyl, 2-pyridyl, and trifluoromethyl are considered to be hydrocarbyl for the purposes of this specification. Hydrocarbyl groups include, but are not limited to aryl, heteroaryl, carbocycle, heterocycle, alkyl, alkenyl, alkynyl, and combinations thereof.

The term "heteroatom", is not particularly limited and should be understood by a skilled worker. As used herein, the term means an atom of any element other than carbon or hydrogen. In one embodiment, for the example and without limitation, heteroatoms include nitrogen, oxygen, silicon and sulfur. The term "alkyl" as used herein is not particularly limited and should be known to a person of skill in the art; and refers to substituted or unsubstituted saturated hydrocarbon groups, including straight-chain alkyl and branched-chain alkyl groups, including haloalkyl groups such as trifluoromethyl and 2,2,2-trifluoroethyl, etc. In one embodiment, for example and without limitation, the alkyl group is a $C_{1-6}$ alkyl.

The term $C_{1-6}$ alkyl in accordance with the specification is not particularly limited and should be known to a person of skill in the art. The $C_{1-6}$ alkyl may be, for example, and without limitation, any straight or branched alkyl, for example, methyl, ethyl, n-propyl, i-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-methylbutyl, 1,2-dimethylbutyl, 1-ethyl-2-methylpropyl, 1,1,2-trimethylpropyl, 1,1-dimethylbutyl, 2,2-dimethylbutyl, 2-ethylbutyl, 1,3-dimethylbutyl, 2-methylpentyl or 3-methylpentyl.

The term "aryl" as used herein is not particularly limited, and should be known to a person of skill in the art. In one embodiment, for example and without limitation, the aryl group is a $C_{6-14}$ aryl. In another embodiment, for example and without limitation, aryl includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Examples of aryl include, for example and without limitation, benzene, toluene, naphthalene, phenanthrene, phenol, aniline, anthracene, and phenanthrene.

A leaving group as disclosed herein is a molecular fragment or stable species that can be detached from a molecule in a bond-breaking step. The leaving group, in accordance with the specification, is not particularly limited and should be known to a person of skill in the art or can be determined. The ability of a leaving group to depart is correlated with the $pK_a$ of the conjugate acid, with lower $pK_a$ being associated with better leaving group ability. Examples of leaving group include, without limitation, halide or a sulfonate. Halides can include, for example, Cl, Br or I. Examples of sulfonates can include, without limitation, nonaflate, triflate, fluorosulfonate, tosylate, mesylate or besylate. In one embodiment, for example and without limitation, the leaving group is chloride, mesylate or tosylate. The functional groups that can be converted into leaving groups, in accordance with the specification, are not particularly limited.

In one embodiment, for example the functional group can be a hydroxyl group that can be converted into a leaving group as described above.

The halide as used herein is not particularly limited and should be known to a person of skill in the art. In one embodiment, for example and without limitation, halides can include, Cl, Br or I. In a further embodiment, the halide is I.

In still another aspect, the specification relates to a process for preparation of halichondrin analogs, including for example, preparation of the compound of formula 3, or a pharmaceutically acceptable salt thereof. The process containing the step of performing an intramolecular cyclization reaction on a compound of formula 1b to form the compound of formula 3, where $R^1$, $R^2$, $R^3$, $R^4$, $R^5$, $R^{10}$, $R^{11}$, $R^{12}$, ----- and $R^{13}$ are as described herein.

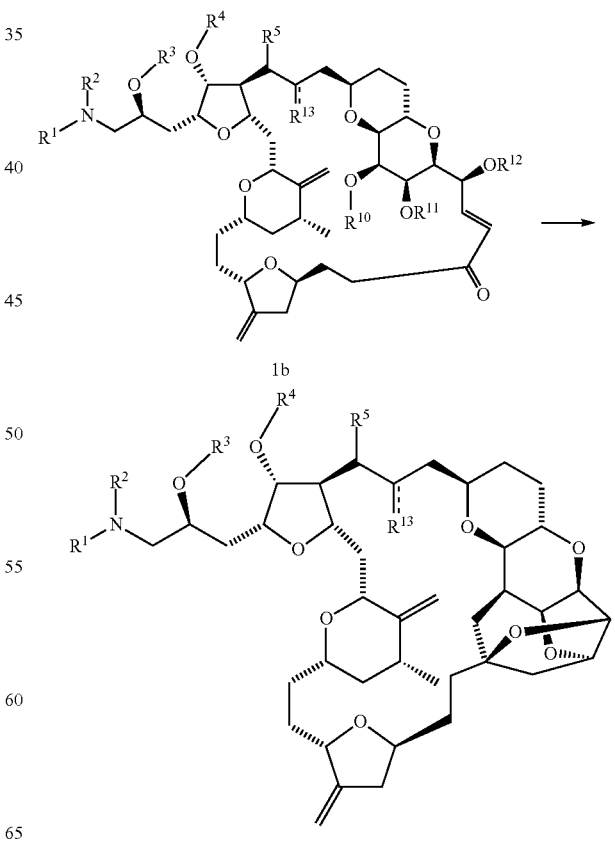

The method of performing the intramolecular cyclization reaction in accordance with the specification is not particularly limited. In one embodiment, for example and without limitation, $R^{10}$, $R^{11}$ and $R^{12}$ are H and the intramolecular cyclization reaction is performed using an acid. The type of acid used is also not particularly limited. In one embodiment, for example and without limitation, the acid is a mild acid that is also non-nucleophilic, and can be, for example but not limited to, pyridinium p-toluenesulfonate (PPTS), trialkyl ammonium sulfate and weak carboxylic acids, such as, for example and without limitation, acetic acid. Following the cyclization reaction, the reaction product can be treated with a base to neutralize the reaction mixture. The base used is not particularly limited. In one embodiment, the base is, for example, cesium carbonate ($Cs_2CO_3$). In addition, alkali metal based bases, such as an alkali metal carbonates, phosphates etc. can also be used.

In still another aspect, the specification relates to a process for preparation of the compound of formula 1, or a pharmaceutically acceptable salt thereof. The process containing the step of coupling a compound of formula 2b with a compound of formula 4 to form the compound of formula 1.

where $R^1$, $R^2$, $R^3$, $R^4$, $R^5$, $R^6$, $R^7$, $R^{7\prime}$, $R^8$, $R^9$, $R^{10}$, $R^{11}$, $R^{12}$, ----- and $R^{13}$ are as described herein; and $R^{13\prime}$ is —C(=O)$R^{22}$, wherein $R^{22}$ is H or $OR^{23}$, wherein $R^{23}$ is H or a hydrocarbon, the hydrocarbon optionally having one or more heteroatoms.

In one embodiment, for example and without limitation, the coupling reaction is performed by use of a base. The base used for the coupling reaction is not particularly limited, and can be determined by a skilled worker. In one embodiment, for example and without limitation, the base is lithium hexamethyldisilazide (LiHMDS), n-butyllithium (BuLi), lithium diisopropylamide (LDA), lithium diethylamide (LDEA), sodium amide ($NaNH_2$) or sodium hydride (NaH). In a further embodiment, the base used is n-butyllithium (BuLi). In a still further aspect, the specification relates to a process for preparation of compound of formula 2, or a pharmaceutically acceptable salt thereof. The process involving coupling a compound of formula 5b with a compound of formula 6, to form the compound of formula 2.

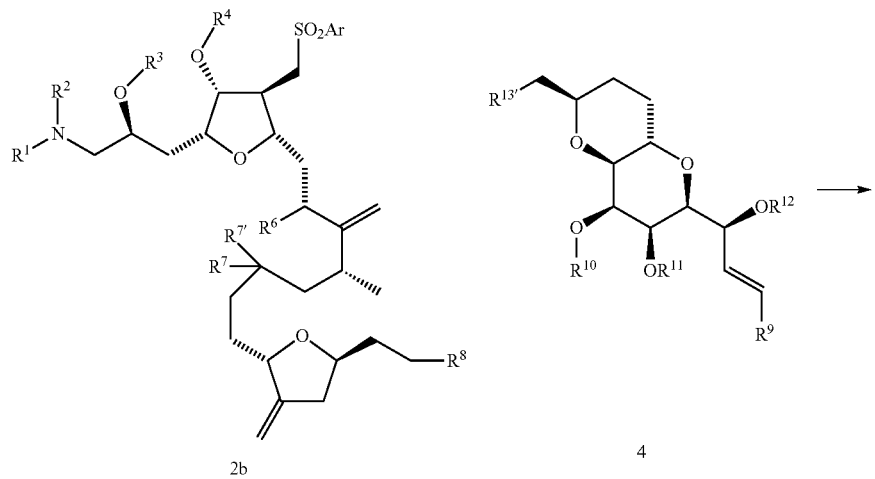

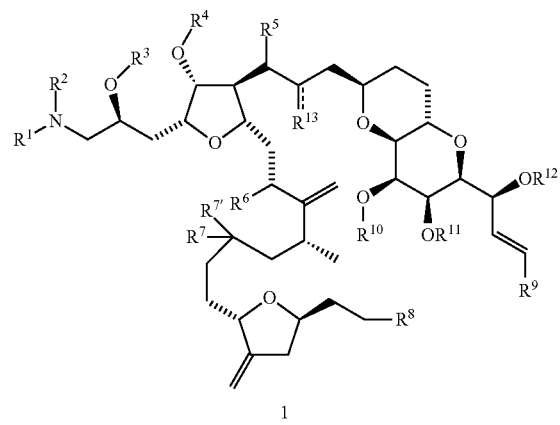

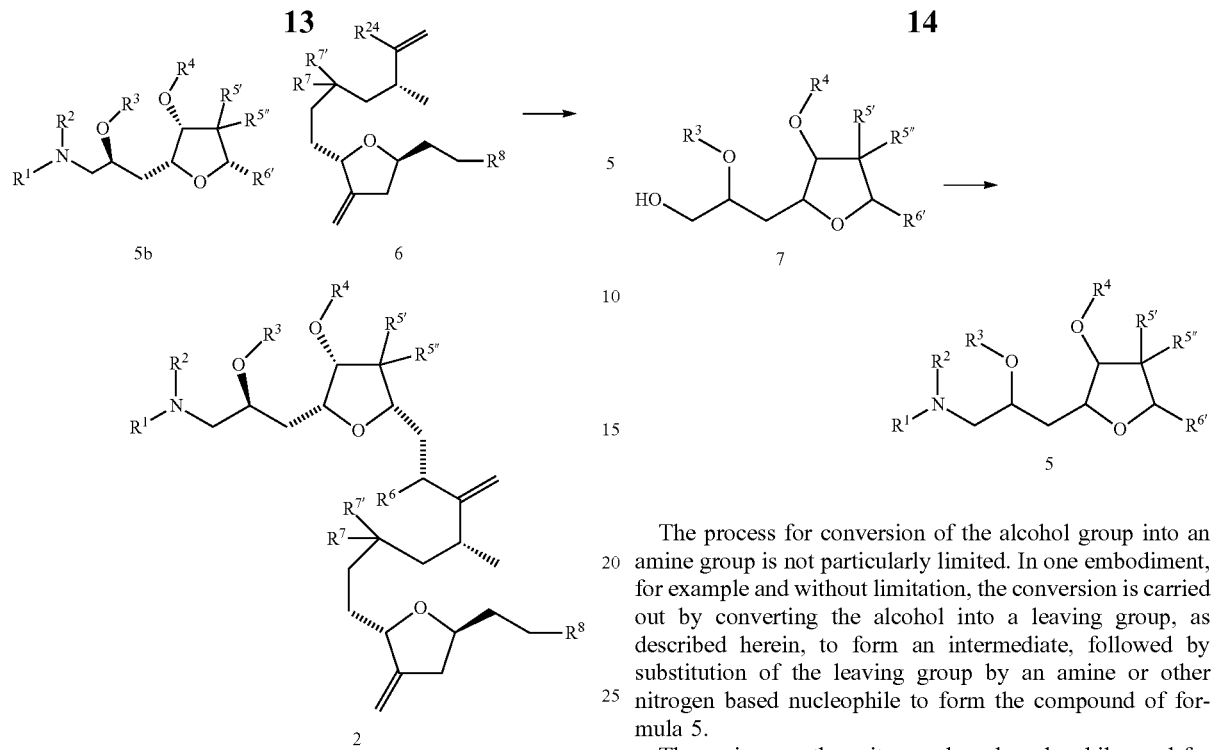

where $R^1$, $R^2$, $R^3$, $R^4$, $R^5$, $R^{5''}$, $R^6$, $R^7$, $R^{7'}$ and $R^8$ are as described herein; and $R^{6'}$ is —$CH_2C(=O)R^{25}$ or —$CH_2CH_2OR^{26}$; wherein $R^{25}$ is H or $OR^{27}$, wherein $R^{27}$ is H or a hydrocarbon, the hydrocarbon optionally having one or more heteroatoms, and $R^{26}$ is H or an alcohol protecting group. And, $R^{24}$ is a halide or a sulfonate.

The method of coupling the compound of formula 5b with the compound of formula 6 is not particularly limited. In one embodiment, for example and without limitation, where $R^{6'}$ is —$CH_2C(=O)H$, the coupling reaction is performed using a nickel/chromium catalyst, such as in the Nozaki-Hiyama-Kishi reaction. In a still further embodiment, for example and without limitation, the catalyst used for the coupling reaction is $NiCl_2/CrCl_2$. In another embodiment, for example and without limitation, the coupling reaction performed is a Grignard reaction.

In still another aspect, the specification relates to a process for preparation of the compound of formula 5, or a salt thereof. The process containing the step of converting the terminal alcohol of the compound of formula 7 into an amine or substituted amine to form the compound of formula 5; where $R^1$, $R^2$, $R^3$ and $R^4$ are as described herein. One of $R^{5'}$ and $R^{5''}$ is H and the other is —$CH_2OR^{28}$ or —$CH_2SO_2$—Ar, or $R^{5'}$ and $R^{5''}$ taken together form =O or =CH—$SO_2$—Ar, wherein $R^{28}$ is H or an alcohol protecting group, and Ar is an aryl group, as described herein. $R^{6'}$ is —$CH_2$—$CH=CR^{29}R^{29'}$, —$CH_2C(=O)$—$R^{25}$ or —$CH_2$—$CH_2$—O—$R^{26}$, wherein $R^{29}$ and $R^{29'}$ each independently is H or a hydrocarbon, the hydrocarbon optionally having one or more heteroatoms; $R^{25}$ is H or $OR^{27}$, wherein $R^{27}$ is H or a hydrocarbon, the hydrocarbon optionally having one or more heteroatoms; and $R^{26}$ is H or an alcohol protecting group.

The process for conversion of the alcohol group into an amine group is not particularly limited. In one embodiment, for example and without limitation, the conversion is carried out by converting the alcohol into a leaving group, as described herein, to form an intermediate, followed by substitution of the leaving group by an amine or other nitrogen based nucleophile to form the compound of formula 5.

The amine or other nitrogen based nucleophile used for formation of the compound of formula 5 is not particularly limited. In one embodiment, for example and without limitation, the amine used for the substitution reaction is ammonia dissolved in an organic solvent. In another embodiment, for example and without limitation, the nitrogen based nucleophile is an azide. The azide used is also not particularly limited, and can be, in one embodiment for example, trimethylsilyl azide ($TMSN_3$).

In one embodiment, the compound formed after amination and where $R^3$ is H, the hydroxyl and amine functional groups of the compound are protected. Alcohol protecting group, as described above, can be used to protect the alcohol group, and where $R^3$ is as described above.

The amine protecting group as used herein is not particularly limited and should be known to a person of skill in the art. In one embodiment, for example and without limitation, amine protecting group can include carbobenzyloxy (Cbz), p-methoxybenzyloxy carbonyl (Moz), tert-butoxycarbonyl (t-BOC), 9-fluorenylmethoxycarbonyl (FMOC), acetyl (Ac), benzoyl (Bz), carbamate, p-methoxybenzyl (PMB), 3,4-Dimethoxybenzyl (DMPM) or p-methoxyphenyl (PMP). In a further embodiment, the amine protecting group is tert-butoxycarbonyl (t-BOC).

In one embodiment, for example, in the compound of formula 5, $R^{6'}$ is —$CH_2$—$CH=CH_2$. In another embodiment, for example, in the compound of formula 5 $R^{6'}$ is —$CH_2$—$C(=O)H$. The process for formation of the compound of formula 5 where $R^{6'}$ is —$CH_2$—$C(=O)H$ is not particularly limited. In one embodiment, the compound of formula 5 where $R^{6'}$ is —$CH_2$—$C(=O)H$ is formed from a compound where $R^{6'}$ is —$CH_2$—$CH=CH_2$. The process for conversion is not particularly limited. In one embodiment, for example and without limitation, the conversion is carried out by oxidatively cleaving the alkene to form the aldehyde.

The process for oxidatively cleaving the alkene to an aldehyde is not particularly limited and should be known to a person of skill in the art or can be determined. In one embodiment, for example and without limitation, the oxidative cleavage is performed using osmium tetroxide/sodium periodate or by ozonolysis.

In one embodiment in the compound of formula 5, one of $R^{5'}$ and $R^{5''}$ is H and the other is —$CH_2OR^{28}$ or —$CH_2SO_2$—Ar, or $R^{5'}$ and $R^{5''}$ taken together form =O or =CH—$SO_2$—Ar, where Ar is aryl and $R^{28}$ is H or an alcohol protecting group. In a further embodiment in the compound of formula 5, one of $R^{5'}$ and $R^{5''}$ is —$CH_2SO_2$—Ph or —$CH_2SO_2$—(p-tolyl). In a still further embodiment, for example, the one of $R^{5'}$ and $R^{5''}$ is —$CH_2SO_2$—Ph or —$CH_2SO_2$—(p-tolyl) and the carbon to which it is attached has the S-configuration.

The process for formation of a compound of formula 5 where $R^{5'}$ and $R^{5''}$, is as described herein, is not particularly limited. In one embodiment, for example a compound of formula 8 is converted into the compound of formula 5, where one of $R^{5'}$ and $R^{5''}$ is —$CH_2SO_2$— Ph or —$CH_2SO_2$—(p-tolyl).

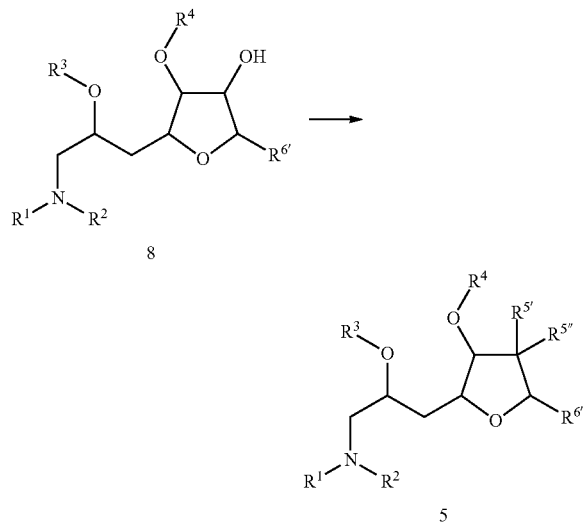

The process for conversion of the alcohol group into $R^{5'}$ and $R^{5''}$, as described above, in the compound of formula 5 is not particularly limited. In one embodiment, for example and without limitation, the alcohol is oxidized to a ketone ("R'—C(=O)—R") prior to conversion to the compound of formula 5. The oxidation of the alcohol is not particularly limited, and should be known to a skilled worker or can be determined. In one embodiment, for example and without limitation, the oxidation is performed using a chromium-based reagent, such as Collins reagent, pyridinium dichromate (PDC) or pyridinium chlorochromate (PCC); activated dimethyl sulfoxide (DMSO), such as, Swern oxidation, Moffatt oxidation or Doering oxidation; or hypervalent iodine compounds, such as, Dess-Martin periodinane or 2-iodoxybenzoic acid.

Following oxidation of the alcohol to a ketone, the ketone functional group can be, in one embodiment, for example and without limitation, converted into an alkene. The reaction to convert a ketone to an alkene is not particularly limited, and should be known to a skilled worker or can be determined. In one embodiment, for example and without limitation, the ketone can be converted into an alkene using the Peterson olefination, the Wittig reaction or the like. In a further embodiment, for example and without limitation, the ketone is converted into an alkene using $(EtO)_2POCH_2SO_2Ph$ or $(i-PrO)_2POCH_2SO_2Ph$.

Upon formation of the alkene, the compound can be reduced to alkane using a reducing agent. The reducing agent used in not particularly limited and can be determined by a skilled worker. In one embodiment, for example and without limitation, the reduction is carried out using a hydride source. The hydride source used is not particularly limited and should be known to a skilled worker or can be determined. In one embodiment, for example and without limitation, the hydride source is Stryker's Reagent ($[(PPh_3)CuH]_6$) or sodium borohydride triacetate ($NaBH(OAc)_3$).

In one embodiment in the compound of formula 5, $R^4$ is H, $C_{1-3}$ alkyl, $C_{1-3}$ haloalkyl or an alcohol protecting group, as described herein. In a further embodiment, for example and without limitation, $R^4$ is $C_{1-3}$ alkyl. In a still further embodiment, for example and without limitation, $R^4$ is methyl.

The description of the molecules disclosed herein has been made using abbreviations that should be known to a skilled worker or can be determined. Some of the abbreviations used include: Ph for phenyl ($C_6H_5$—), Ar for aryl, which has been described herein, Ac for acetyl ($CH_3C(=O)$—), t-Bu for tert-butyl (($CH_3)_3C$—), $Et_3N$ for triethylamine (($CH_3CH_2)_3N$), CDI for 1,1'-carbonyldiimidazole $PPh_3$ for triphenylphosphine (($C_6H_5)_3P$), Et for ethyl ($C_2H_5$—), $SO_2Ph$ for —$SO_2C_6H_5$, Me for methyl ($CH_3$—), MeO for methoxy ($CH_3O$), MeOH for methanol ($CH_3OH$), TBSO=OTBS=TBDMSO=OTBDMS for tert-butyldimethylsiloxy ((($CH_3)_3C)(CH_3)_2SiO$)—, $Boc_2O$ is for tert-butyl pyrocarbonate, $NaIO_4$ is for sodium periodate, $TMSN_3$ is for trimethylsilyl azide, Bn is for benzyl ($C_6H_5CH_2$—), TMSI is for trimethylsilyliodide (($CH_3)_3SiI$), KHMDS is for potassium hexamethyldisilazide, TBAF is for tetra-butyl ammonium fluoride, mCPBA is for meta-chloroperoxybenzoic acid, DMAP is for dimethylaminopyridine, TsCl is for tosyl chloride, and DMF is for dimethylformamide.

The process for preparation of compounds of formula 5 will now be described with reference to Scheme 1 and 2, shown below.

Scheme 1

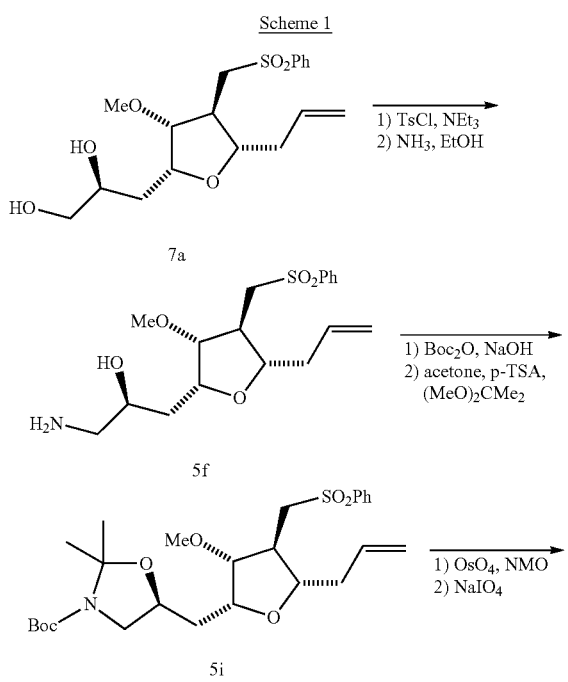

-continued

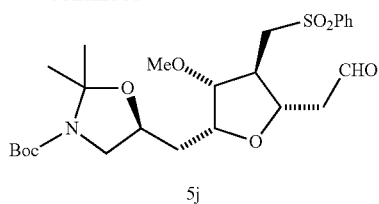

5j

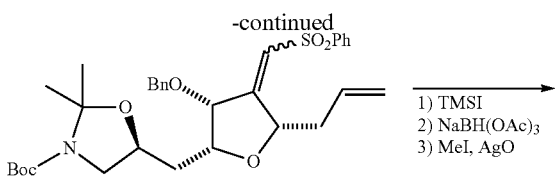

5m

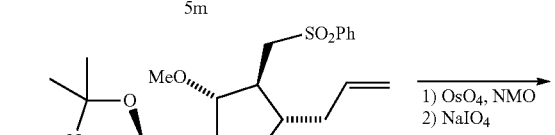

5i

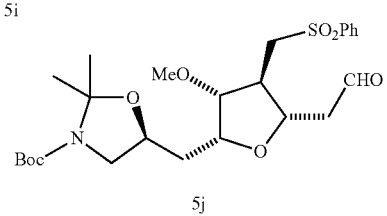

5j

The compound of formula 7a, as shown in Scheme 1, can be obtained from D-(+)-Glucurono-6,3-lactone according to the conditions as described in PCT patent application number WO 2005/118535, incorporated herein by reference. The terminal alcohol in the compound of formula 7a can be converted into a leaving group, such as a tosylate, followed by nucleophillic substitution with an amine, such as ammonia, that leads to formation of the compound of formula 5f. Reaction with di-tert-butyl pyrocarbonate ($Boc_2O$) and subsequent formation of an acetonide leads to the compound of formula 5i. The alkene in the compound of formula 5i can then be oxidized to an aldehyde of formula 5j, by oxidation using osmium tetroxide and N-methyl morpholine N-oxide, followed by reaction with sodium periodate ($NaIO_4$).

Scheme 2 discloses an alternate route for the synthesis of compounds of formula 5. Formation of the epoxide of formula H can be carried out following a similar procedure as disclosed in Org. Lett., 2010, 12, 744, incorporated herein by reference. Nucleophillic reaction of the compound of formula H with an azide, such as trimethylsilyl azide ($TMSN_3$) can lead to the formation of compound of formula J. The azide can be reduced using, for example and without limitation, triphenylphosphine ($PPh_3$), followed by reaction of the amine with $Boc_2O$ and acetone/2,2-dimethoxypropane, as described above in Scheme 1, to form the compound of formula K. Nucleophillic reaction with, for example and without limitation, allyltrimethylsilyl in the presence of a catalyst, of the compound of formula K leads to compound of formula L.

The catalyst used for such for such nucleophillic reaction is not particularly limited and can be determined by a skilled worker. In one embodiment, for example and without limitation, the catalyst used is $Ti(OPr^i)Cl_3$.

The alcohol group in the compound of formula L can be oxidized to a ketone, followed by a Wittig or Homer-Wadsworth Emmons type reaction to form the compound of formula 5m. The benzyl group (Bn) from the compound of formula 5m is removed using trimethylsilyl iodide (TMSI) to provide a free hydroxyl group. The arylsulfonyl alkene can be reduced using a hydride source, for example and without limitation, $NaBH(OAc)_3$. As shown in scheme 2, the reduction of the double bond by $NaBH(OAc)_3$, with a vicinal free hydroxyl group can help to direct the reduction process and to obtain the desired stereoselectivity of the arylsulfonylmethyl moiety. The free hydroxyl is then methylated to form the compound of formula 5i. Oxidative cleavage of the alkene functional group in the compound of formula 5i with, for example and without limitation, osmium tetroxide and N-methylmorpholine N-oxide followed by sodium periodate leads to the formation of compound 5j.

The compound of formula 5, as disclosed herein, can be used for the preparation of compounds of formula 1, 2 or 3. In one embodiment, the synthesis of such compounds is disclosed in Schemes 3 and 4.

In Scheme 3, the compound of formula 5j is coupled to a compound of formula 6a to form the compound of formula 2c. Synthesis of the compounds, similar to the compound of

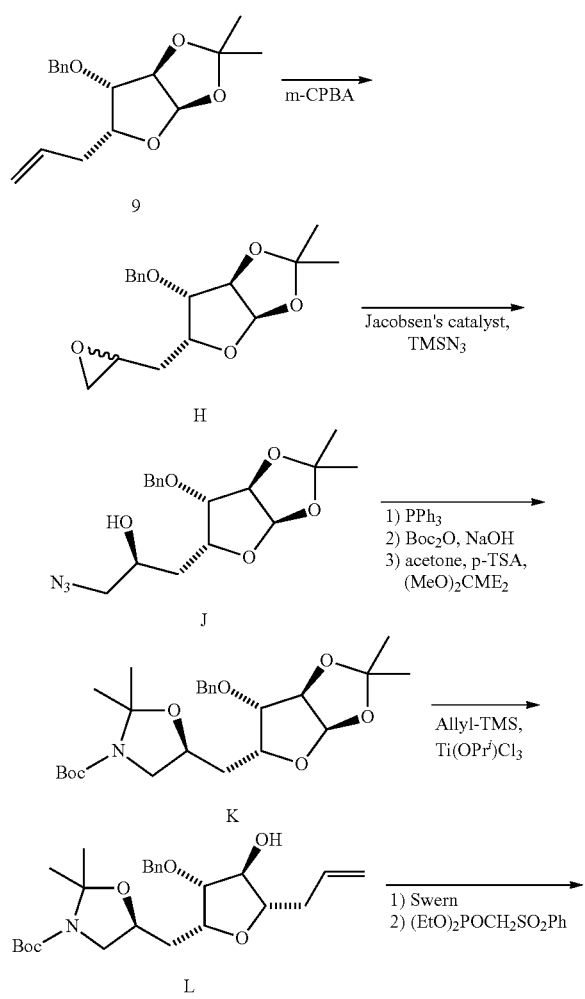

formula 6a are described in PCT International Publication Number WO 2005/118565 A1, Guo, H. et al. J. Am. Chem. Soc., 2009, 131, 15387-93, Kim, D-S. et al. J. Am. Chem. Soc., 2009, 131, 15636-641, and Choi, H-w. et al. Org. Lett., 2002, v. 4 (25), 4435-38 (all incorporated herein by reference). In the embodiment shown, the coupling reaction is performed using a Ni/Cr catalyst, with the conditions for the coupling reaction being similar to those disclosed in U.S. Pat. No. 6,214,865 B1 or Kim, D-S. et al. J. Am. Chem. Soc., 2009, 131, 15636-641 (all incorporated herein by reference). Following coupling, displacement of the chloride can be achieved to form the tetrahydropyran ring. The reagent used is not particularly limited, and in the embodiment shown, the reagent is silver tetrafluoroborate ($AgBF_4$).

Scheme 3

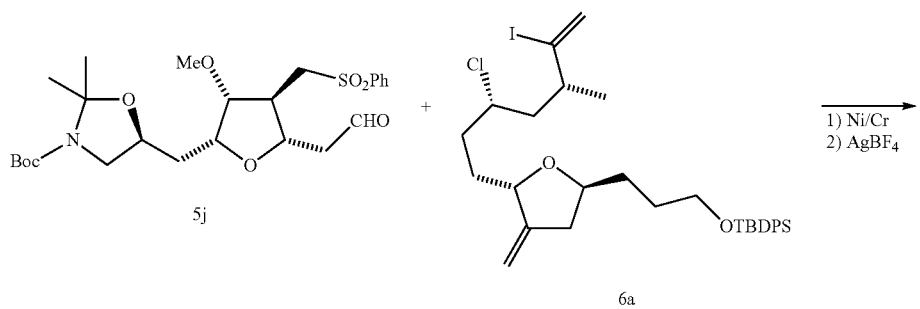

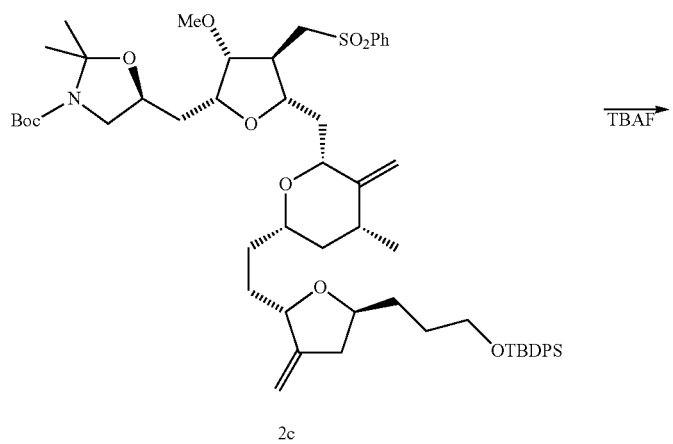

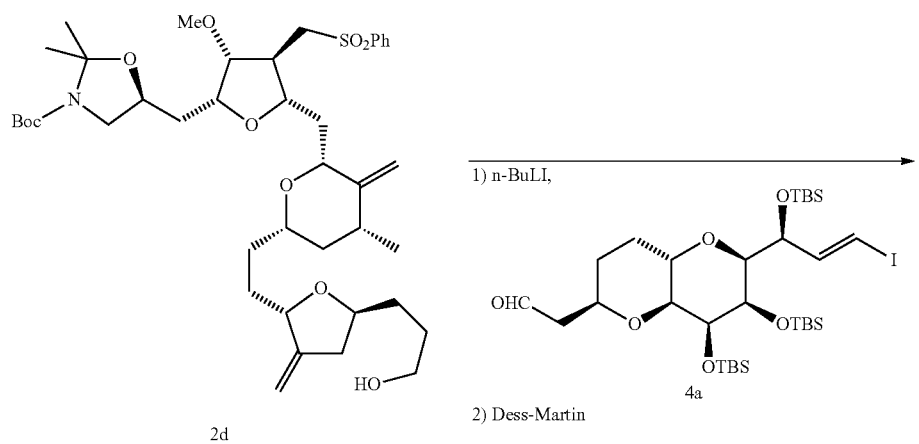

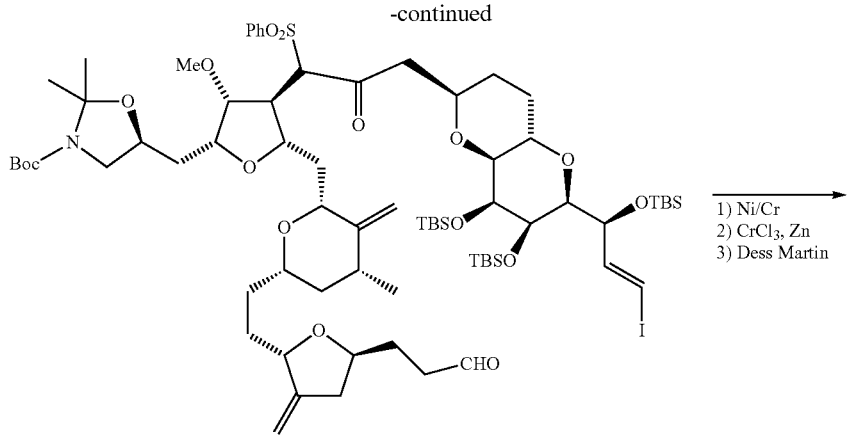

1c

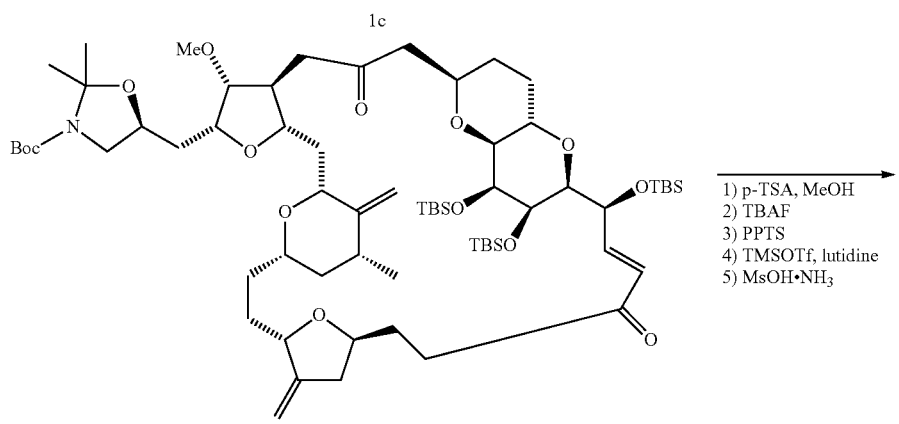

1d

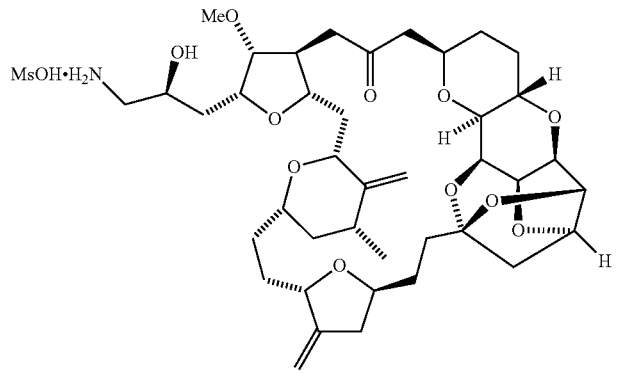

Eribulin mesylate, 3

The compound of formula 2c can be desilylated using conditions that should be known to a skilled worker. In the embodiment disclosed, the desilylation is performed by tetra-butyl ammonium fluoride (TBAF), to obtain the compound of formula 2d. Coupling of the compound of formula 2d with the compound of formula 4a can be performed under basic conditions, similar to those as noted herein and disclosed in U.S. Pat. No. 6,214,865 B1 (incorporated herein by reference) to form an intermediate alcohol. Oxidation of the alcohol using reagents as noted-above results in formation of the compound of formula 1c.

The compound of formula 1c is subjected to an intramolecular coupling reaction, under conditions similar to those involved in the coupling of compound of formula 5j with 6a, followed by reduction of the arylsulfonyl moiety using a reducing agent, for example and without limitation, trivalent chromium and zinc. Subsequent oxidation using reagents as described above, can be performed to obtain compound of formula 1d.

Desilylation of the compound of formula 1d can be performed using reagents known to a skilled person. For example and without limitation, desilylation is performed using a fluoride source. In one embodiment, for example and without limitation, the desilylation is performed using tetra-butyl ammonium fluoride (TBAF). Intramolecular cyclization of the resultant alcohol intermediate can be performed under acidic conditions, similar to those disclosed in U.S. Pat. No. 6,214,865 to form eribulin.

The formation of the salt of eribulin (3) or compounds of formula 1 and 2 are not particularly limited. The salt formed can be used for isolation and purification of the compound; and can lead to a product having higher purity and/or reduced amount of impurities. In one embodiment, for example and without limitation, the eribulin is reacted with an acid under conditions that should be known to a person of skill in the art or can be determined to form the desired salt. In a further embodiment, eribulin is reacted with methanesulfonic acid to form the eribulin mesylate salt.

In an alternate embodiment, as shown in Scheme 4, the compound of formula 5q is coupled with a compound of formula 6b. The coupling reaction can be performed, as described above. In one embodiment, for example and without limitation, the coupling reaction is performed using asymmetric conditions, using a nickel-chromium catalyst. Deprotection of the resulting compound and intramolecular cyclization results in formation of the compound of formula 2c.

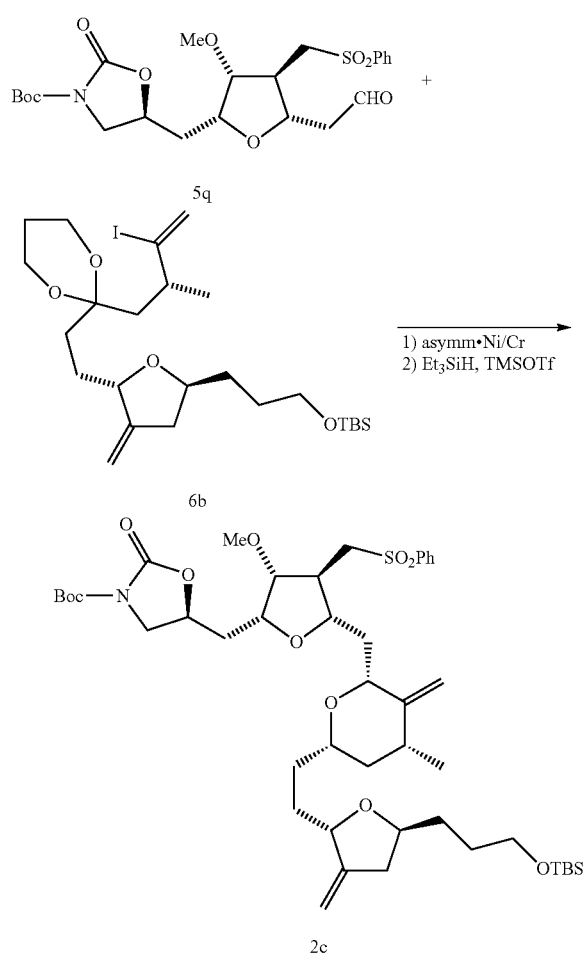

Scheme 4

The organic solvent used in the reactions described herein is not particularly limited and should be known to a person of skill in the art or can be determined. The particular solvent used would depend upon the reactants and the reaction being carried out, to allow the reaction to proceed.

Tubulin Polymerization Assays:

Biological activity of Halichondrin B, Eribulin, halichondrin B analogs and Eribulin analogs for example can be determined according to the methods described in Cancer Research, 2001, 61: 1031-1021 (incorporated herein by reference). In detail the polymerization of bovine brain tubulin in vitro can be assessed and compared with reference substances. The substance of interest can be dissolved in anhydrous DMSO and further diluted in 10% DMSO, 90% PEM buffer (PEM-buffer: 80 mM PIPES [Piperazine-N,N'-bis(2-ethanesulfonic acid)],pH 6.9, 1 mM EGTA (ethylene glycol tetraacetic acid), 1 mM magnesium chloride). Test samples can be prepared by combining in a total volume of 100 μk 3 mg/ml bovine brain tubulin (Cytoskeleton, Inc, Denver, Colo., USA), 1 mM ATP, 3% (volume/volume) glycerol, 1% DMSO in PEM-buffer. The polymerization reaction can be initiated by raising the temperature from 4° C. to 37° C. over a period of 3 minutes. Readout of the assay is the tubulin polymerization as determined for example by measuring the absorbance at 340 nm, measured over time for example once every minute for 60 minutes (Cancer Research, 61, page 1014, left row, paragraph 3 and FIG. 6 on page 1018).

A similar assay is described in Journal of Biological Chemistry, 1985, 26: 2819-2825 (incorporated herein by reference).

Cell Growth Inhibition Assays:

Cell growth inhibition assays are also described in Cancer Research, 2001, 61: 1031-1021 (incorporated herein by reference). Biological activity on viable human cancer cells for example can be shown by use of cell lines representing different types of human cancer, such as COLO 205 and DLD-1 (colon cancer), DU 145 and LNCaP (prostate cancer), HL-60 (promyelocytic leukemia), U937 (histiocytic lymphoma), MDA-MB-435 (human breast cancer), and LOX (human melanoma). These cells can be obtained from the American Type Culture Collection (ATCC), Rockville, Md., USA) or from the Division of Cancer Treatment-NCI Tumor Repository (Frederick, Md., USA) (LOX-cell line), or from Dr. Mary J. C. Hendrix, University of Iowa College of Medicine, Iowa City, Iowa, USA) (MDA-MB-435 cell line, MDA-MB-4355 available from ATCC). All cell lines can be grown at 37° C., 5% carbon dioxide at empirically optimized cell densities. All cell lines can be cultured under tissue culture conditions as recommended by ATCC. LOX cell line can be cultured in RPMI 1640 medium, 10% heat-inactivated fetal bovine serum, 2mM L-glutamine, MDA-MB-435 cell line can be cultured in DMEM (high glucose), 10% heat-inactivated fetal bovine serum, 20 mM N-2-hydroxyethyl-piperazine-N'-2-ethanesulfonic acid, 1 mM sodium pyruvate.

For the biological cell growth inhibition assay, cells can be seeded in 96-well plates at 7,500 cells/well (except LNCaP, which can be seeded at 10,000 cells/well). All cells can be grown for 4 days in the presence of said substances of interest. Subsequently in order to quantitate cell numbers, sterile-filtered 3-(4,5-dimethylthiazol-2yl)-2,5-diphenyl tetrazolium bromide can be added to each well resulting in a final concentration of 0.5 mg/ml, incubation for 4 h at 37° C., addition of 150 μl 0.1 N HCl in isopropanol, gentle mixing and measurement of absorbance at 540 nm. Details of this method are described in Cancer Research, 61, 1031-1021, page 1013, last paragraph to page 1014 first paragraph, as well as in FIG. 2 and table 1 of the same publication. Furthermore this technique is described in Analytical Biochemistry, 1984, 139: 272-277, and in Journal of Immunological Methods, 1983, 65: 55-63 (all incorporated herein by reference).

For comparison reference substances such as the microtubule destabilizer vinblastine and the microtubule stabilizer paclitaxel can be used in in vitro tubulin polymerization or in cell growth inhibition tests.

Determination of Purity by HPLC:

Determination of the purity of Halichondrin B, Eribulin, Halichondrin B analogs and Eribulin analogs for example can be determined by High Pressure Liquid Chromatography (HPLC) as known in the art. The substance of interest is dissolved in a suitable solvent, for example in an organic solvent such as ethanol and subjected to HPLC. The elution profile of the substance of interest and of any potential impurities or degradation products is recorded. The percentage of purity of the substance of interest for example can then be calculated by determining the area below the peak of the substance of interest and separately the area below the peaks of all other substances eluted from the HPLC column. Alternatively the peak of the substance of interest and separately all other peaks can be collected, the HPLC-elution buffer be removed (for example by evaporation if the buffer is an organic solvent such as ethanol), thereby enabling weighing of the eluted substance of interest and the eluted other substances in order to calculate percentage of purity of the substance of interest.

EXAMPLES

The invention is now described by way of examples, which disclose embodiments of the inventions, and are not intended to be limiting of the invention as described and claimed herein.

Example 1

Preparation of Compound of Formula H'

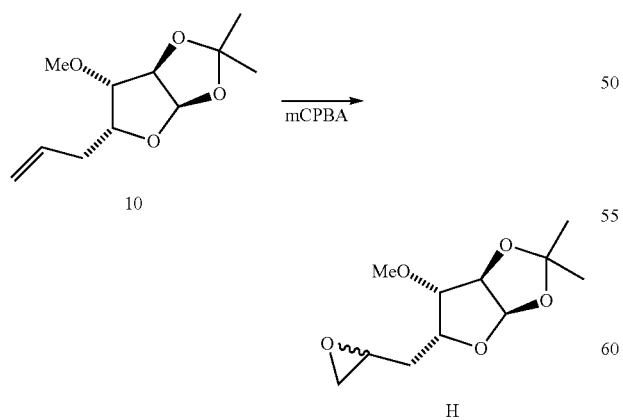

Epoxide of formula H' was prepared by oxidation of compound of formula 10 with mCPBA, following the procedure described in *Org. Lett.* 2010, 12, 744.

Example 2

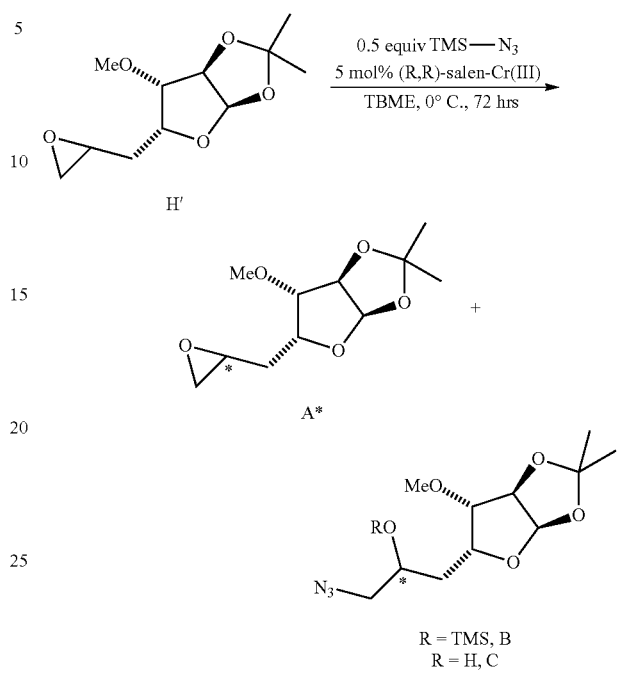

A dry reaction vessel equipped with a stir bar and rubber septum, under an atmosphere of $N_2$, was charged with compound H' (1 wt). Compound H' was dissolved in anhydrous methyl t-butyl ether (1.6 v) and the resulting solution was cooled to 0° C. (R,R)-salen-Cr(III) (0.01 eq, 0.03 wt) and TMSN$_3$ (0.50 eq, 0.25 wt) were added to the solution of H' at 0° C. and the resulting reaction mixture was stirred at 0° C. for 72 hrs. The volatiles were removed under reduced pressure and the crude mixture was separated by column chromatography (SiO$_2$, 1:0-7:13 heptanes:EtOAc) to afford single isomers A* (0.49 eq) and B+C (0.49 eq) as colourless oils.

Example 3

Preparation of Compound of Formula 7a

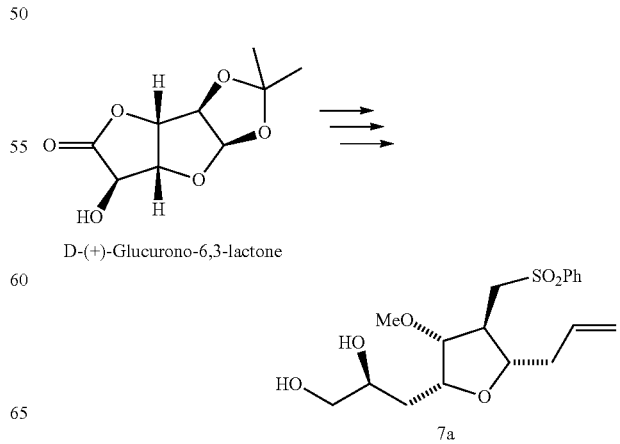

The diol of formula 7a was prepared from D-(+)-Glu-curono-6,3-lactone according to the conditions described in PCT publication number WO 2005/118565.

Example 4

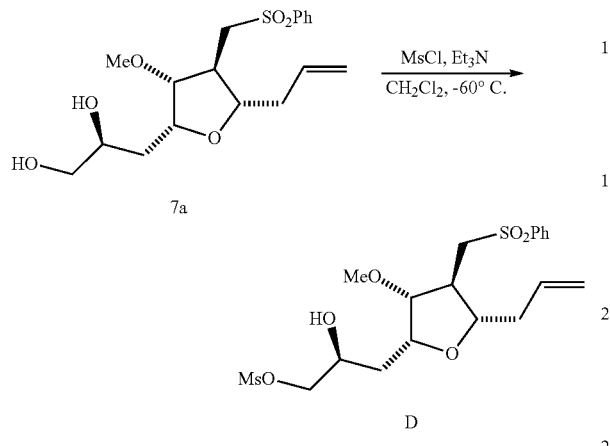

Compound 7a (1 wt.) is dissolved in CH$_2$Cl$_2$ (14 v) and the resulting solution is cooled to an internal temperature of −60° C. Et$_3$N (1.1 eq., 0.3 wt.) and MsCl (1.1 eq., 0.3 wt) are added sequentially at −60° C. The internal temperature of the reaction mixture is kept below −52° C. The reaction is run at −60° C. for 45 min, until no further conversion is detected by TLC (1:1 heptanes:EtOAc). The reaction is quenched with water (5 v), warmed to room temperature and the organic layer is separated. The aqueous layer is further extracted with CH$_2$Cl$_2$ (2×5 v) and the combined organic layers are dried over Na$_2$SO$_4$, filtered and concentrated in vacuo. The crude mixture is purified by column chromatography (SiO$_2$, 1:0-1:1 heptanes:EtOAc) to afford compound of formula D.

Example 5

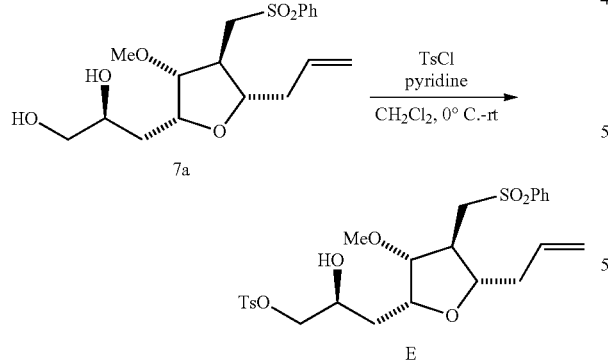

Compound 7a (1 wt.) is dissolved in CH$_2$Cl$_2$ (5.7 v) and the resulting solution is cooled to 0° C. To the solution of 7a is added pyridine (5.0 eq., 1.1 wt.), catalytic DMAP and TsCl at 0° C. The reaction mixture is allowed to slowly warm to room temperature and is stirred at room temperature until TLC analysis (1:1 heptanes:EtOAc) indicates the reaction to be complete. The reaction is quenched with sat. aq. NH$_4$Cl (5 v). The organic layer is separated and washed once more with sat. aq. NH$_4$Cl, followed by 1M HCl. The organic layer is dried over Na$_2$SO$_4$, filtered and concentrated in vacuo. The crude product is purified by column chromatography (SiO$_2$, 3:1-1:1 heptanes:EtOAc) to obtain E.

Example 6

Preparation of Compound of Formula 5f

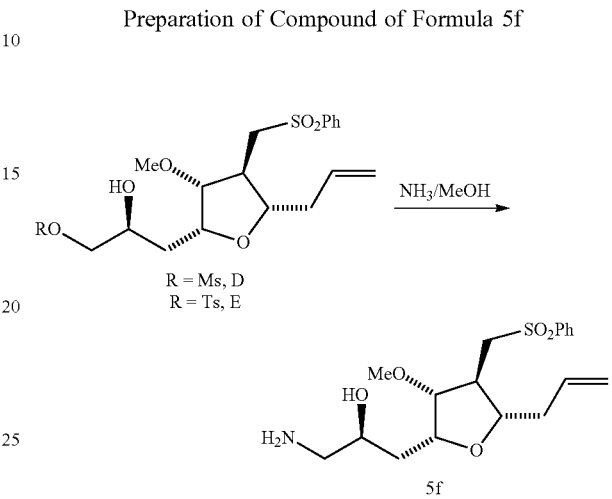

Compound D or E (1 wt.). is dissolved in 7 N NH$_3$ in methanol (33 v) and stirred at room temperature for 3 days, or until TLC analysis (1:1 heptanes:EtOAc) indicates that the starting material is consumed. The volatiles are removed in vacuo and the crude mixture is redissolved in CH$_2$Cl$_2$ and washed with sat. aq. NaHCO$_3$. The organic layer is separated, dried over Na$_2$SO$_4$, filtered and concentrated in vacuo to afford crude 5e which is used without further purification.

Example 7

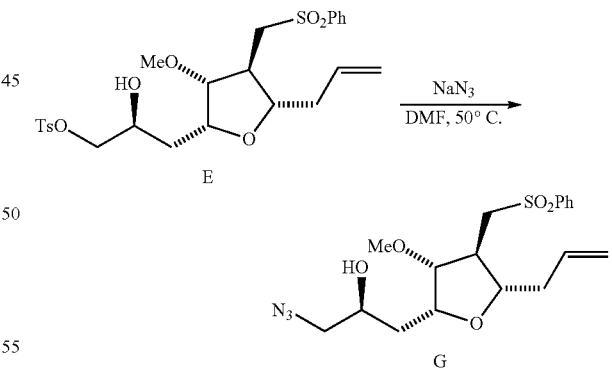

Compound E (1 wt) is dissolved in DMF (20 v) and to this solution is added NaN$_3$ (6.5 eq. 0.82 wt) at room temperature. The reaction mixture is heated to 50° C. until TLC analysis (1:1 heptanes:EtOAc) indicates the starting material to be consumed. The reaction mixture is quenched with water, diluted with diethyl ether and the layers are separated. The aqueous layer is further extracted with diethyl ether and the combined organics are dried over Na$_2$SO$_4$, filtered and concentrated in vacuo. The crude product G is used without further purification.

Example 8

Preparation of the Compound of Formula 5f

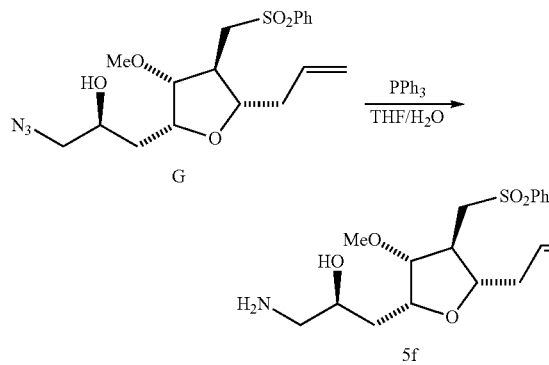

Crude product G (1 wt) is dissolved in THF (10 v) and to this solution is added PPh$_3$ (1.1 eq. 0.58 wt.) and water (1 v). The reaction mixture is stirred at room temperature until TLC analysis (1:1 heptanes:EtOAc) indicates that the starting material has been consumed. The reaction is quenched with water and diluted with EtOAc. The layers are separated and the aq. layer is extracted twice more with EtOAc. The combined organics are dried over Na$_2$SO$_4$, filtered and concentrated to afford crude 5f, which is used without purification.

Example 9

Preparation of Compound of Formula 5g

Compound E (1 wt) is dissolved in DMF (20 v) and to this solution is added potassium phthalimide (3.0 eq. 1.1 wt) at room temperature. The reaction mixture is stirred at room temperature until TLC analysis (1:1 heptanes:EtOAc) indicates that the starting material is consumed. The reaction mixture is quenched with water, diluted with diethyl ether and the layers are separated. The aqueous layer is further extracted with diethyl ether and the combined organics are dried over Na$_2$SO$_4$, filtered and concentrated in vacuo. The crude product is purified by column chromatography (SiO$_2$, 1:0-1:1 heptanes:EtOAc) to afford 5g.

Example 10

Preparation of Compound of Formula 5h

Compound 5f (1 wt.) is dissolved in CHCl$_3$ (11 v) and to the resulting solution Et$_3$N (1.5 eq., 0.42 wt.) and CDI (1.5 eq., 0.33 wt.) are added. The reaction mixture is stirred at room temperature until TLC analysis (95:5 CH$_2$Cl$_2$:MeOH) shows that the starting material has been consumed. The reaction mixture is diluted with CH$_2$Cl$_2$ and washed twice with water and once with brine. The organic layer is dried over Na$_2$SO$_4$, filtered and concentrated. The crude product is purified by column chromatography (SiO$_2$, 9:1-6:4 CH$_2$Cl$_2$:acetone) to afford 5h.

Example 11

Preparation of Compound of Formula 5p

Compound 5h (1 wt.) is dissolved in THF (71 v) and to this solution are added Et$_3$N (1.2 eq, 0.29 wt.), catalytic DMAP and Boc$_2$O (1.3 eq., 0.71 wt.) at room temperature. The reaction is stirred at room temperature until TLC analysis (8:2 CH$_2$Cl$_2$:acetone) shows that the starting material has been consumed. The reaction mixture is diluted with EtOAc and washed sequentially with water and 1 M HCl. The organic layer is dried over Na$_2$SO$_4$, filtered and concentrated to afford crude 5p, which is used without further purification.

Example 12

Preparation of Compound 5q

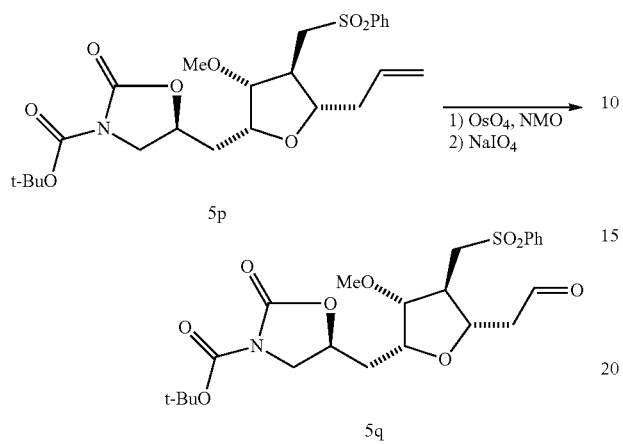

To a solution of alkene 5p (1.28 mmol) in $CH_2Cl_2$ (8 mL) at room temperature is added 4-methylmorpholine N-oxide (3.84 mmol, 3.0 equiv) and a solution of $OsO_4$ (0.10M in $H_2O$, 0.020 equiv). The resulting mixture is vigorously stirred for 1.5h and 0.5M aqueous solution of sodium bisulfite (10 mL) is then added. After stirring for 30 min at room temperature, the mixture is extracted with $CH_2Cl_2$ (10 mL×3) and the combined organic layers are washed with brine (10 mL), dried over $MgSO_4$, filtered and concentrated under vacuum. The resulting residue is dissolved in $CH_2Cl_2$ (10 mL) and a saturated $NaHCO_3$ aqueous solution (0.25 mL) is added, followed by slow addition of $NaIO_4$ (3.84 mmol, 3.0 equiv) with vigorous stirring. After stirring for 5 h at room temperature, the reaction mixture is filtered and the resulting filtrate is concentrated under vacuum to give crude compound 5q.

Example 13

Preparation of Compound of Formula 5k

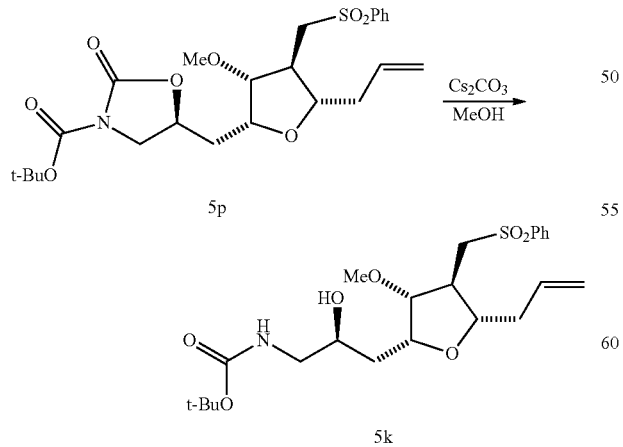

Compound 5p (1 wt.) is dissolved in MeOH (32 v) and to this solution is added $Cs_2CO_3$ (0.2 eq, 0.13 wt.) at room temperature. The reaction is stirred at room temperature until TLC analysis (8:2 $CH_2Cl_2$:acetone) shows that the starting material has been consumed. The reaction mixture is partitioned between water and EtOAc and the organic layer is separated. The aqueous layer is extracted twice more with EtOAc and the combined organics are dried over $Na_2SO_4$, filtered and concentrated in vacuo to afford 5k.

Example 14

Preparation of Compound E-1C

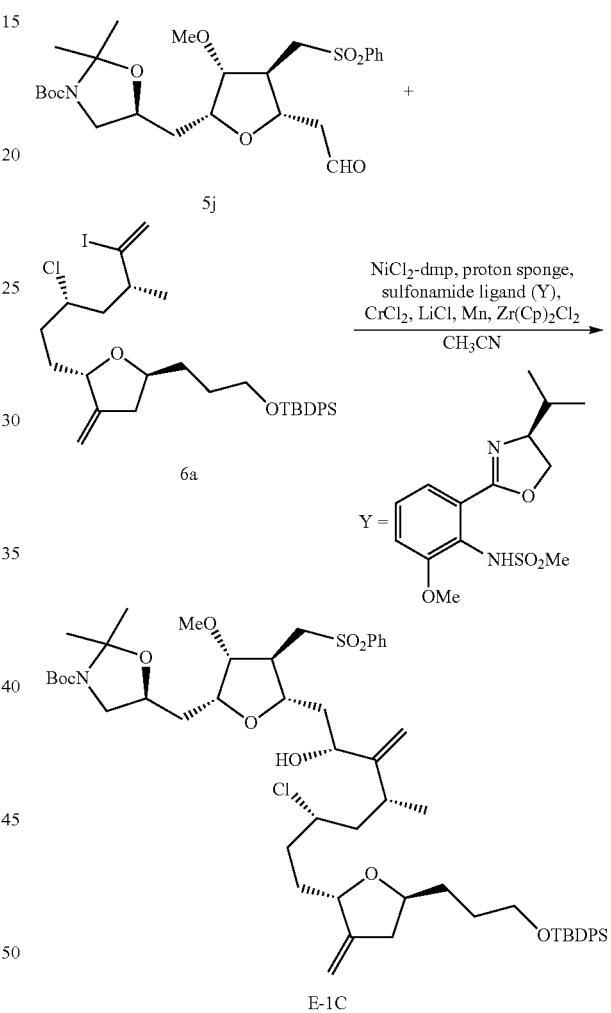

All reagents and solvents are stored in a glovebox. Substrates 5j and 6a are azeotropically dried 2× with toluene, before introduction into the glovebox. A 100 mL round-bottom flask equipped with a stir bar was oven dried and cooled under inert atmosphere during introduction to the glovebox. To a 100 mL round-bottom flask equipped with a stir bar, under inert atmosphere, were added $CrCl_2$ (655 mg, 5.33 mmol, 1.0 eq), sulfonamide ligand Y(1.83 g, 5.86 mmol, 1.1 eq) and proton sponge (1.26 g, 5.86 mmol, 1.1 eq). The solid reagents were suspended in acetonitrile (25 mL), producing a dark blue-green solution, which was stirred vigorously at room temperature for 1 hour. To the dark blue-green solution, lithium chloride (452 mg, 10.66 mmol, 2.0 eq), manganese (586 mg, 10.66 mmol, 2.0 eq), Zr(Cp)$_2$Cl$_2$ (1.71 g, 5.86 mmol, 1.1 eq) and a complex of nickel(II) chloride with 2,9-dimethyl-1,10-phenanthroline (NiCl$_2$·dmp) (36 mg, 0.11 mmol, 0.02 eq) were added, followed by a suspension of 6a (3.47 g, 5.33 mmol, 1.0 eq) and 5j (4.09 g, 7.99 mmol, 1.5 eq) in acetonitrile (25 mL). The reaction vessel was capped and stirred vigorously for 16 hours. Another portion of lithium chloride (452 mg, 10.66 mmol, 2.0 eq) and NiCl$_2$·dmp (36 mg, 0.11 mmol, 0.02 eq) were added and the reaction was left stirring at room temperature for 4 hours more. The reaction mixture was then poured into a suspension of florisil (<200 mesh, 90 g) in methyl tert-butyl ether (MTBE) (300 mL) and stirred at room temperature (rt) for 1 hour. The mixture was filtered over silica gel and rinsed with MTBE and several times with 8/2 dichloromethane/acetone. The filtrate was concentrated and subsequently purified by column chromatography using a Biotage Isolera, 100 g Snap column and 5-10% acetone in dichloromethane as eluent. The product E-1C was afforded as a white foam (4.5 g, 82%) and used as is.

Example 15

Preparation of Compound 2c

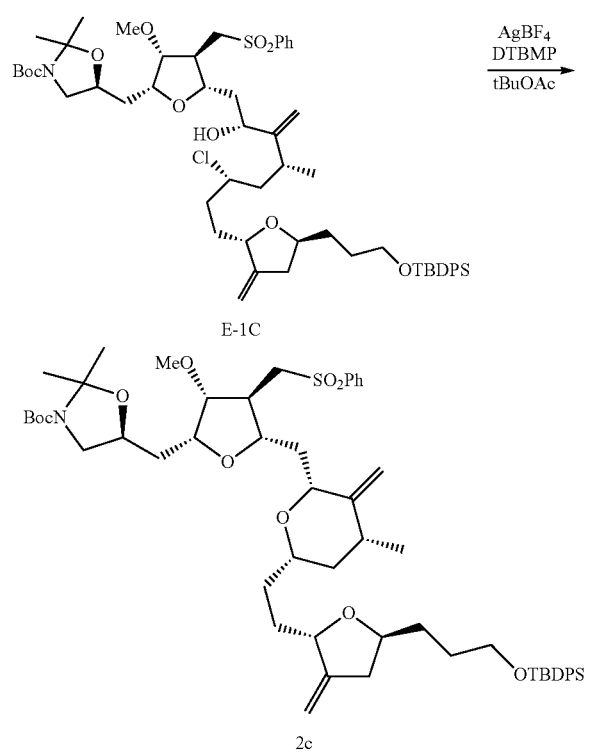

Compound E-1C (4.12 g, 3.97 mmol, 1.0 eq.) was dissolved in tert-butyl acetate (tBuOAc) (200 mL) and the resulting solution was cooled to 0° C., under N$_2$. 2,6-Di-tert-butyl-4-methylpyridine (DTBMP) (4.08 g, 19.85 mmol, 5.0 eq) was added, followed by silver tetrafluoroborate (2.32 mg, 11.92 mmol, 3.0 eq). The reaction flask was immediately removed from the cold bath, wrapped in aluminum foil and left stirring at room temperature for 16 hours. The reaction was quenched with saturated aqueous ammonium chloride solution (150 mL). The resulting mixture was extracted with MTBE (3×100 mL), dried over MgSO$_4$, filtered and concentrated to afford a colourless oil. The crude product was purified by column chromatography using Biotage Isolera, 100 g Snap column and 0-10% acetone in dichloromethane to afford the product 2c as a white foam (3 g, 76%).

Example 16

Preparation of Compound 2d

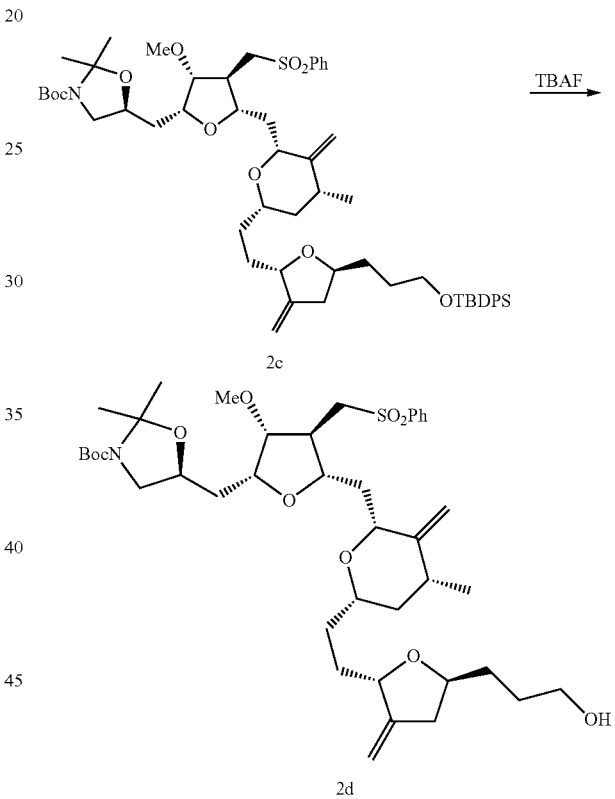

Compound 2c (3 g, 3.0 mmol, 1.0 eq) was dissolved in anhydrous tetrahydrofuran (THF) (40 mL), at room temperature, under N$_2$. Tetrabutylammonium fluoride (TBAF) (1M in THF, 3.9 mL, 3.9 mmol, 1.3 eq) was added in one portion and the reaction mixture was stirred at room temperature for 16 hours. The reaction was quenched with saturated aqueous ammonium chloride solution (50 mL) and the mixture was extracted with MTBE (3×50 mL). The combined organic layers were dried over MgSO$_4$, filtered and concentrated. The crude product was purified by column chromatography using a Biotage Isolera, 100 g Snap column and 10-30% acetone in dichloromethane as an eluent. The product 2d was afforded as a white foam (2.15 g, 94%), which upon drying could be handled like a solid.

Example 17

Preparation of Compound 1c

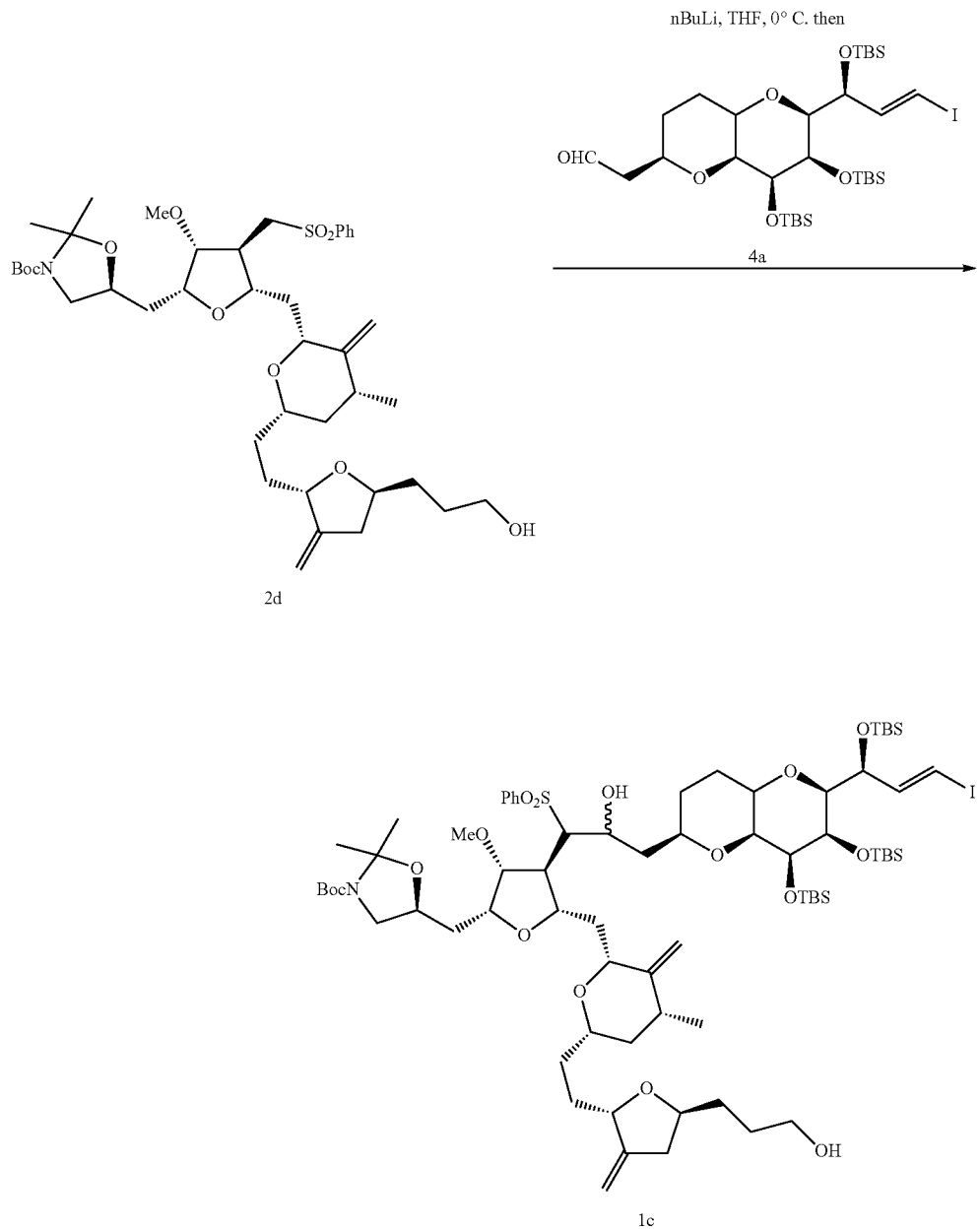

Compound 2d (955 mg, 1.25 mmol, 1.0 eq.) was dissolved in THF (13 mL) and the solution was cooled to 0° C. Butyl lithium (nBuLi) (1.5M in THF) was added dropwise until the bright yellow colour of the sulfone anion was just visible and persisted (1.12 mL) and a second aliquot of nBuLi (0.84 mL, 1.25 mmol, 1.0 eq) was then added to the reaction mixture. The resulting yellow solution was stirred at 0° C. for 10 min and then cooled to −70° C. Compound 4a (1.39 g, 1.88 mmol, 1.5 eq) was dissolved in hexanes (20 mL) and added to the reaction mixture, which was stirred at −70° C. for an additional 45 min. The cooling bath was removed and reaction was quenched with the addition of saturated aqueous ammonium chloride solution (20 mL) and the resulting mixture was extracted with MTBE (3×20 mL). The combined organic layers were washed with brine (20 mL), dried over MgSO$_4$, filtered and concentrated. The crude material was purified by column chromatography using a Biotage Isolera, 100 g Snap Ultra column and 5-20% acetone in dichloromethane as an eluent. 1c was obtained as a white foam (1.46 g, 77%).

Example 18

Preparation of Compound E-6C

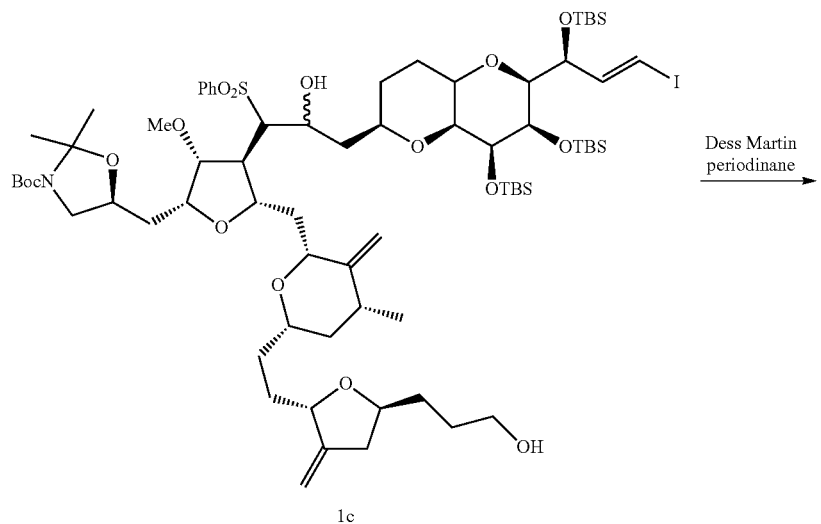

1c

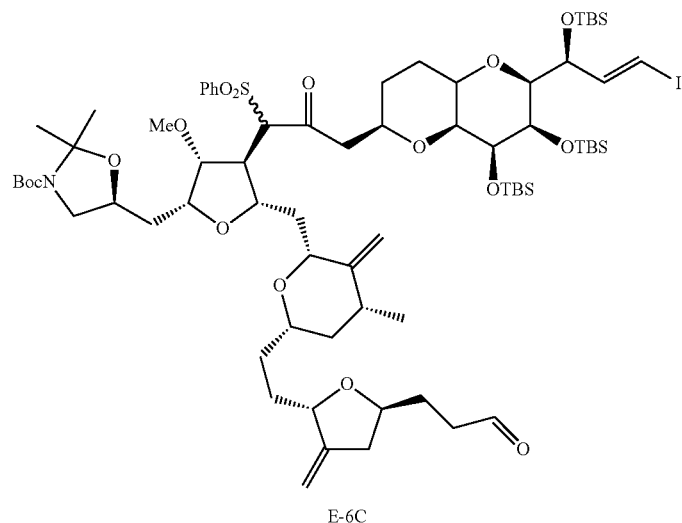

E-6C

Compound 1c (2.71 g, 1.80 mmol, 1.0 eq.) was dissolved in dichloromethane (20 mL) at room temperature. Dess Martin periodinane (1.91 g, 4.51 mmol, 2.5 eq) was added in one portion and the reaction mixture was stirred for 1.5 hours. The reaction was quenched by the addition of saturated aqueous sodium bicarbonate solution (15 mL) and 10% (w/w) sodium thiosulfate solution (15 mL) and further diluted with MTBE (20 mL). The resulting mixture was stirred for 30 min, diluted with brine (15 mL) and the layers were separated. The aqueous phase was further extracted with MTBE (2×15 mL) and the combined organic layers were washed with brine (15 mL), dried over MgSO$_4$, filtered and concentrated. The crude product was purified by column chromatography using a Biotage Isolera, 100 g Snap column and 5-10% acetone in dichloromethane as an eluent. The product E-6C was afforded as a white foam (1.96 g, 73%).

Example 19

Preparation of Compound E-8C

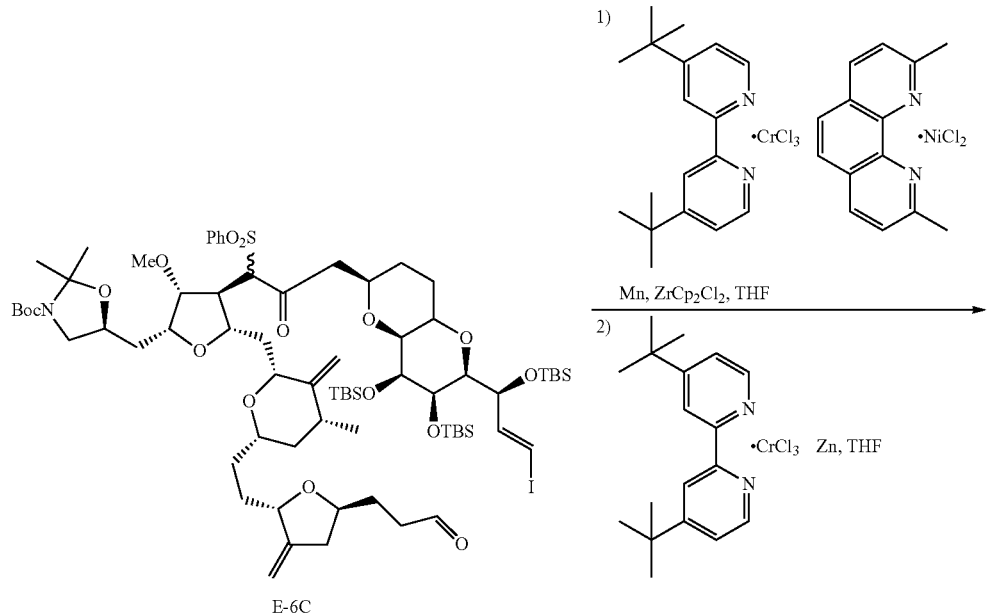

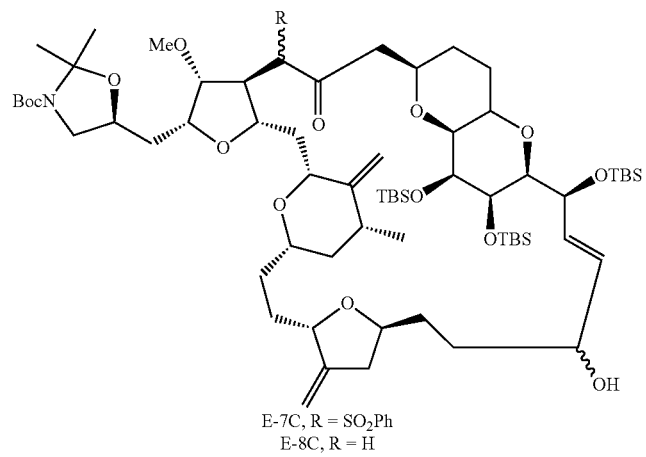

E-7C, R = SO₂Ph
E-8C, R = H

All reagents are stored in a glovebox. A 250 mL round-bottom flask equipped with a stir bar was oven dried and cooled under inert atmosphere during introduction to the glovebox. To a 250 mL round-bottom flask equipped with a stir bar, under inert atmosphere, were added $CrCl_3 \cdot 3THF$ (427 mg, 1.14 mmol, 1.0 eq), 4,4'-tert-butyl-2,2'-bipyridyl (303 mg, 1.14 mmol, 1.0 eq), $NiCl_2 \cdot dmp$ (77 mg, 0.23 mmol, 0.2 eq), manganese (251 mg, 4.56 mmol, 4.0 eq) and $Zr(Cp)_2Cl_2$ (500 mg, 1.71 mmol, 1.5 eq). The reaction vessel was sealed with a rubber septum and brought outside the glovebox. Anhydrous THF (50 mL) was added to the round bottom flask and the resulting mixture was stirred at room temperature for 30 minutes.

Compound E-6C (1.71 g, 1.14 mmol, 1.0 eq.) was dissolved in anhydrous THF (50 mL) and added to the reaction mixture dropwise at room temperature and allowed to stir for 16 hours. The reaction mixture was then poured into a slurry of florisil (50 g) in MTBE (500 mL) and stirred for 30 minutes. The mixture was filtered over celite, rinsed with MTBE followed by 8/2 dichloromethane/acetone (400 mL) and concentrated to afford a mixture of the products E-7C/E-8C (~1:3) as a brown oil (1.48 g).

A 500 mL round-bottom flask was charged with E-7C/E-8C mixture from two different lots (1.27 mmol, 1.0 eq), equipped with a stir bar and introduced into a glovebox. To the reaction vessel were added $CrCl_3 \cdot 3THF$ (2.86 g, 7.62 mmol, 6.0 eq), 4,4'-tert-butyl-2,2'-bipyridyl (3.07 g, 11.43 mmol, 9.0 eq) and Zn (2.51 g, 38.1 mmol, 30.0 eq). The round-bottom flask was sealed with a rubber septum and brought outside the glovebox. Anhydrous THF (125 mL) was added to the reaction mixture and stirred at room temperature for 16 hours. The solvent was then removed under reduced pressure. The residue was suspended in dichloromethane, filtered over silica gel (109 g) with 5-20% acetone in dichloromethane as an eluent to afford the product as a green foam (1.47 g) which was carried on to the next step as is.

Example 20

Preparation of Compound 1d

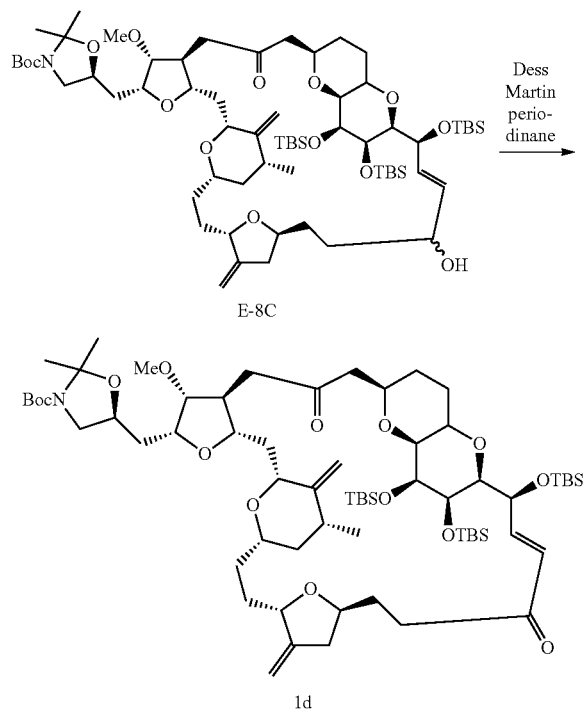 [SMILES: C=C1C[C@@H]2CCC(O)/C=C/[C@H](O[Si](C)(C)C(C)(C)C)[C@@H]3OC4CC[C@H](CC(=O)C[C@@H]5[C@@H](OC)[C@@H](C[C@H]6CN(C(=O)OC(C)(C)C)C(C)(C)O6)O[C@H]5C[C@H]5O[C@@H](CC[C@@H]1O2)C[C@@H](C)C5=C)O[C@@H]4[C@H](O[Si](C)(C)C(C)(C)C)[C@@H]3O[Si](C)(C)C(C)(C)C ; C=C1C[C@@H]2CCC(=O)/C=C/[C@H](O[Si](C)(C)C(C)(C)C)[C@@H]3OC4CC[C@H](CC(=O)C[C@@H]5[C@@H](OC)[C@@H](C[C@H]6CN(C(=O)OC(C)(C)C)C(C)(C)O6)O[C@H]5C[C@H]5O[C@@H](CC[C@@H]1O2)C[C@@H](C)C5=C)O[C@@H]4[C@H](O[Si](C)(C)C(C)(C)C)[C@@H]3O[Si](C)(C)C(C)(C)C]

Compound E-8C (1.47 g, 1.19 mmol, 1.0 eq.) was dissolved in dichloromethane (12 mL) at room temperature. Dess Martin periodinane (759 mg, 1.79 mmol, 1.5 eq) was added in one portion and the reaction mixture was stirred for 1.5 hours. The reaction mixture was loaded directly on a 100 g Snap column for chromatography by Biotage Isolera using 5-10% acetone in dichloromethane as an eluent. Product 1d was afforded as a white foam (750 mg, 48% over 3 steps).

Example 21

Preparation of Compound E-10C

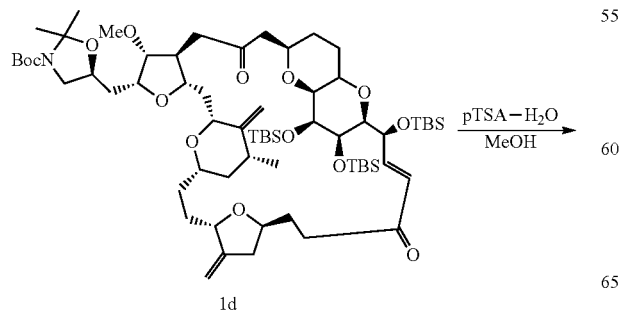

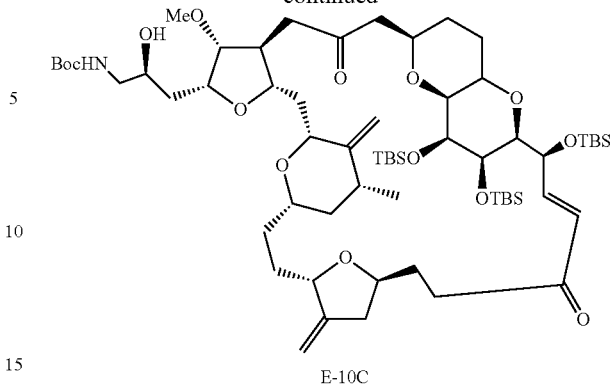

Compound 1d (415 mg, 340 μmol, 1.0 eq) was dissolved in MeOH (7 mL). p-Toluenesulfonic acid monohydrate (13 mg, 68 μmol, 0.2 eq) was added in one portion at room temperature and the reaction was stirred at room temperature for 4 hours. The reaction mixture was diluted with dichloromethane and quenched with sat. aq. sodium bicarbonate solution (10 mL). The layers were separated and the aqueous phase was extracted twice more with dichloromethane (2×15 mL). The combined organic layers were washed with water (15 mL), brine (15 mL), dried over $MgSO_4$, filtered and concentrated to afford a crude E-10C that was carried on to the next step as is.

Example 22

Preparation of Compound E-12A

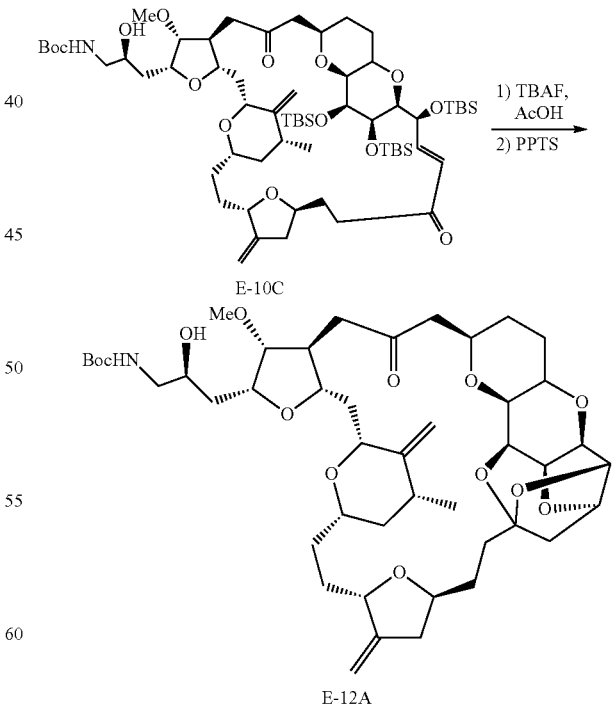

Compound E-10C (340 μmol, 1.0 eq) was dissolved in anhydrous THF (10 mL) at room temperature, under $N_2$. Acetic acid (58 μL, 1.02 mmol, 3.0 eq) was added, followed by a solution of TBAF (1M in THF, 2.0 mL, 2 mmol, 6 eq). The reaction mixture was stirred for 20 hours. Calcium carbonate (408 mg, 4.08 mmol, 12.0 eq) and Dowex 50WX8-400 resin (1.23 g) were added to the reaction mixture and stirring was continued for 1 hour. The reaction mixture was diluted with ethyl acetate and filtered over celite. The solvent was removed under reduced pressure and the residue was dissolved in dichloromethane and filtered over a plug of silica gel using 1/1 dichloromethane/acetone. The solvent was removed under reduced pressure and the residue was dissolved in anhydrous dichloromethane (15 mL). PPTS (427 mg, 1.7 mmol, 5.0 eq) was added and the reaction mixture was stirred at room temperature for 1.5 hours. Half of the reaction mixture was applied directly to a 25 g Snap column for chromatography using a Biotage Isolera and 30-60% MTBE in dichloromethane as an eluent. The product E-12A was afforded as a colourless oil (85 mg, 60%, 3 steps).

Example 23

Preparation of Eribulin

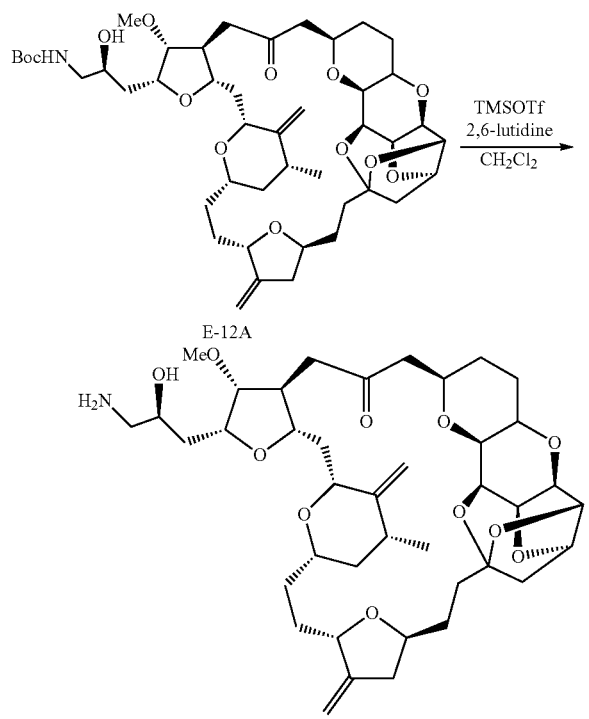

Compound E-12A (133 mg, 160 µmol, 1.0 eq) was dissolved in anhydrous dichloromethane (20 mL) and cooled to 0° C. To this solution was sequentially added 2,6-lutidine (0.09 mL, 0.8 mmol, 5.0 eq), and trimethyl silyl triflate (TMSOTf) (0.12 mL, 0.64 mmol, 4.0 eq) and the cooling bath was removed. The reaction was stirred at room temperature for 1.5 hours and another portion of 2,6-lutidine (5.0 eq) and TMSOTf (4.0 eq) were added at room temperature. The reaction was further stirred for 1 hour and quenched with water (10 mL). The layers were separated and the organic phase was washed with additional water (2×10 mL), brine (10 mL), dried over MgSO$_4$ and concentrated under reduced pressure. The residue was dissolved in MeOH (10 mL), a catalytic amount of K$_2$CO$_3$ was added at room temperature and the resulting mixture was stirred for 2 hours. The reaction was diluted with dichloromethane and quenched with water (10 mL). The layers were separated and the aqueous phase was further extracted with dichloromethane (5×10 mL). The combined organic layers were washed with brine (20 mL), dried over MgSO$_4$, filtered and concentrated. The residue was dissolved in dichloromethane and purified by column chromatography on silica gel, using 1:9 MeOH:CH$_2$Cl$_2$ to 1:9:90 NH$_4$OH:MeOH:CH$_2$Cl$_2$ as eluent. The product was afforded as a white amorphous solid (103 mg, 88%).

Example 23

Preparation of Compound of Formula 4a

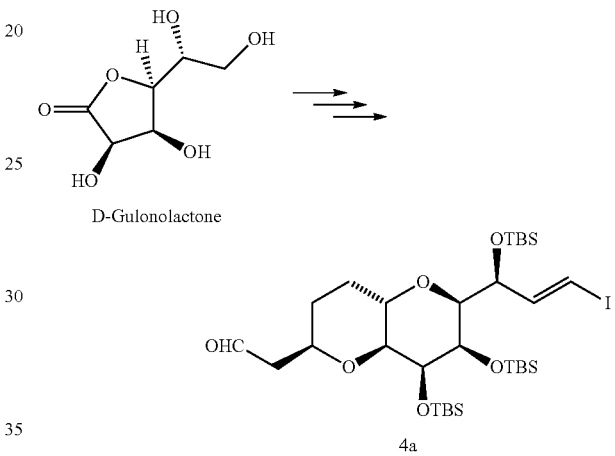

The compound of formula 4a was prepared from D-Gulonolactone according to the conditions described in PCT publication number WO 2005/118565.

Example 24

Preparation of Eribulin Mesylate (3)

Eribulin mesylate (3) was prepared from Eribulin according to the conditions described in U.S. patent application publication number U.S. 2011/0184190.

Example 25

Preparation of Compound of Formula E-1B

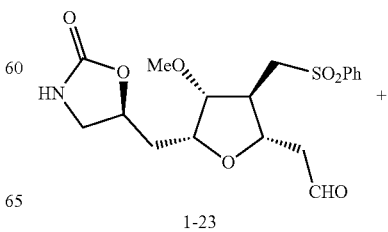

-continued

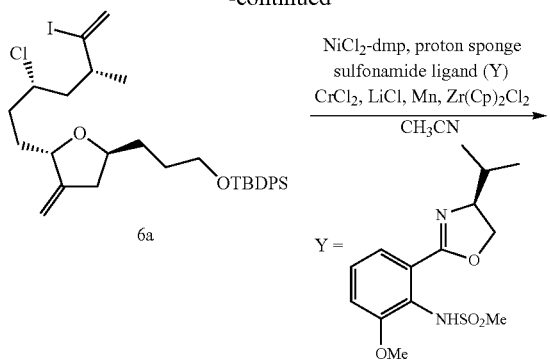

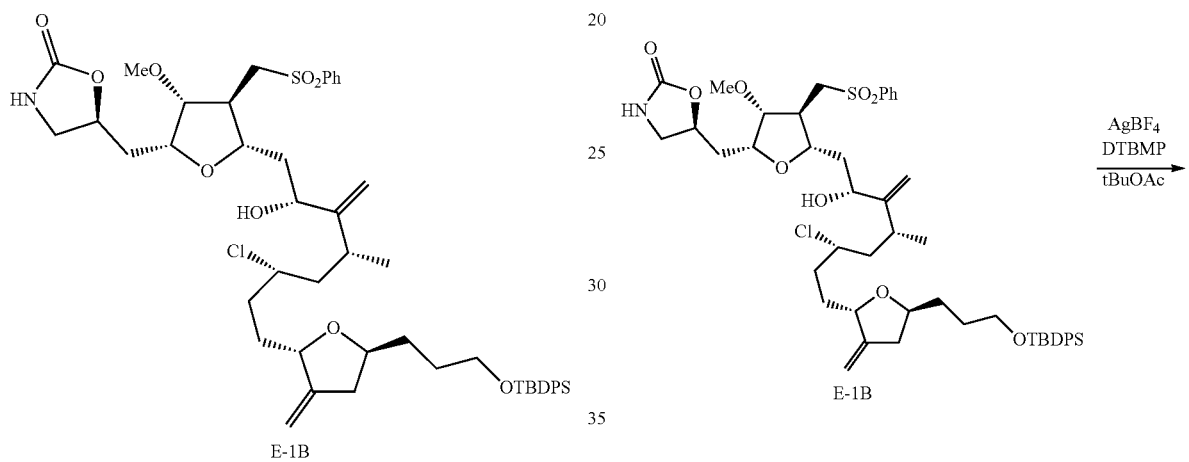

All reagents and solvents are stored in a glovebox. Substrates 1-23 and 6a are azeotropically dried 2x with toluene, before introduction into the glovebox. A 50 mL round-bottom flask equipped with a stir bar was oven dried and cooled under inert atmosphere during introduction to the glovebox. To a 50 mL round-bottom flask equipped with a stir bar, under inert atmosphere, were added CrCl$_2$ (296 mg, 2.41 mmol, 1.0 eq), sulfonamide ligand (829 mg, 2.65 mmol, 1.1 eq) and proton sponge (568 mg, 2.65 mmol, 1.1 eq). The solid reagents were suspended in acetonitrile (11 mL), producing a dark blue-green solution, which was stirred vigorously at room temperature for 1 hour. To the dark blue-green solution, lithium chloride (204 mg, 4.82 mmol, 2.0 eq), manganese (265 mg, 4.82 mmol, 2.0 eq), Zr(Cp)$_2$Cl$_2$ (775 mg, 2.65 mmol, 1.1 eq) and NiCl$_2$·dmp (16 mg, 0.05 mmol, 0.02 eq) were added, followed by a suspension of 6a (1.57 g, 2.41 mmol, 1.0 eq) and 1-23 (1.44 g, 3.62 mmol, 1.5 eq) in acetonitrile (11 mL). The reaction vessel was capped and stirred vigorously for 1-2 hours. Another portion of lithium chloride (204 mg, 4.82 mmol, 2.0 eq) and NiCl$_2$·dmp (16 mg, 0.05 mmol, 0.02 eq) were added and the reaction was left stirring at room temperature for 16 hours. The reaction mixture was then poured into a suspension of florisil (<200 mesh, 30 g) in ethyl acetate (200 mL) and stirred at room temperature (rt) for 1 hour. The mixture was filtered over silica gel and rinsed several times with ethyl acetate. The filtrate was concentrated and subsequently purified by column chromatography on silica gel using 0-30% acetone in dichloromethane as eluent. The product E-1B was afforded as a grey foam (970 mg, 43%) and used as is.

Example 26

Preparation of Compound of Formula E-3A

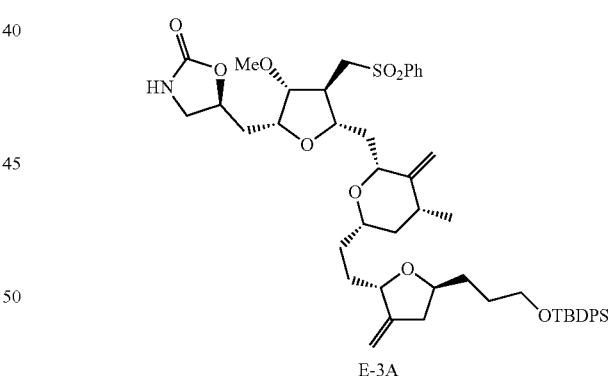

Compound E-1B (970 mg, 1.05 mmol, 1.0 eq.) was dissolved in tBuOAc (100 mL) and the resulting solution was cooled to 0° C., under N$_2$. 2,6-Di-tert-butyl-4-methylpyridine (1.08 g, 5.25 mmol, 5.0 eq) was added, followed by silver tetrafluoroborate (610 mg, 3.15 mmol, 3.0 eq). The reaction flask was immediately removed from the cold bath, wrapped in aluminum foil and left stirring at room temperature for 16 hours. The reaction was quenched with saturated aqueous ammonium chloride solution (100 mL). The resulting mixture was extracted with MTBE (3×50 mL), washed with brine (75 mL), dried over MgSO$_4$, filtered and concentrated. A gummy grey solid remaining in the bottom of the reaction flask was dissolved in dichloromethane (50 mL) and washed with saturated aqueous ammonium chloride solution (30 mL). The second organic layer was also dried over MgSO$_4$, filtered and combined with the first lot of material for concentration. The crude product was purified by column chromatography on silica gel using 10-20% acetone in dichloromethane to afford the product E-3A as a grey foam (693 mg, 74%).

Example 27

Preparation of Compound of Formula E-4A

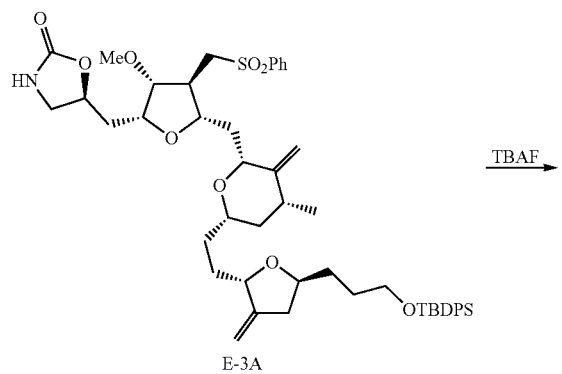

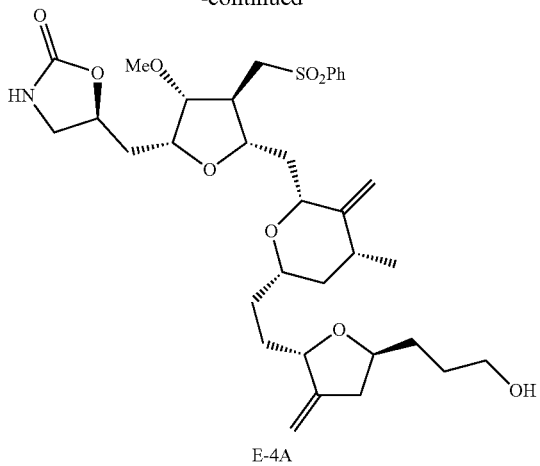

Compound E-3A (693 mg, 0.78 mmol, 1.0 eq) was dissolved in anhydrous THF (8 mL), at room temperature, under N$_2$. Tetrabutylammonium fluoride (1M in THF, 0.86 mL, 0.86 mmol, 1.1 eq) was added in one portion and the reaction mixture was stirred at room temperature for 3 hours. The reaction was quenched with saturated aqueous ammonium chloride solution (10 mL) and the mixture was extracted with MTBE (3×10 mL). The combined organic layers were dried over MgSO$_4$, filtered and concentrated. The crude product was purified by column chromatography on silica gel using 20-50% acetone in dichloromethane as an eluent. The product E-4A was afforded as a white foam (432 mg, 86%), which upon drying could be handled like a solid.

Example 28

Preparation of Compound of Formula E-5A

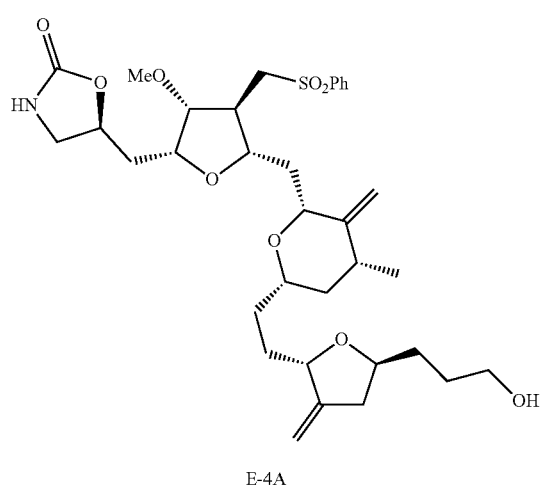

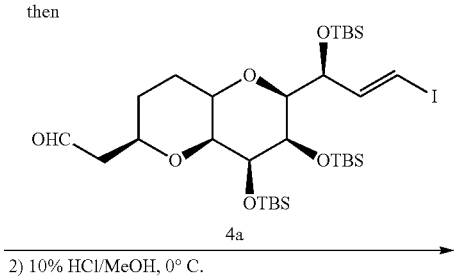

-continued

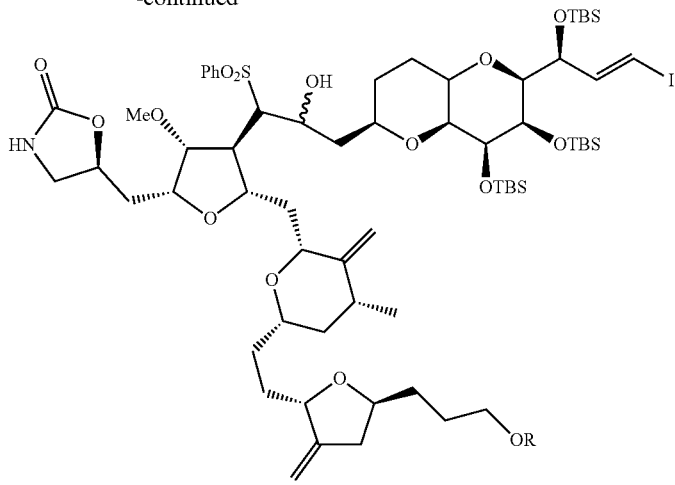

E-5A R = H
E-5Ab R = TMS

Compound E-4A (249 mg, 0.38 mmol, 1.0 eq.) was dissolved in THF (4 mL) and the solution was cooled to 0° C. Lithium diisopropylamide (LDA) (0.5M in THF, 1.61 mL, 0.81 mmol, 2.1 eq) was added dropwise and the reaction mixture was stirred at 0° C. for 10 min. A solution of TMSCl (1M in THF, 0.85 mL, 0.85 mmol, 2.2 eq) was added at 0° C. and the solution was stirred for another 10 min. A second portion of LDA (0.5M in THF, 0.92 mL, 0.46 mmol, 1.2 eq) was added and the reaction mixture was stirred for another 10 min at 0° C. Compound 4a (394 mg, 0.53 mmol, 1.4 eq) was dissolved in THF (3 mL) and added to the reaction mixture, which was stirred at 0° C. for an additional 30 min. The reaction was quenched with the addition of saturated aqueous ammonium chloride solution (10 mL) and the resulting mixture was extracted with MTBE (3×10 mL). The combined organic layers were washed with brine (20 mL), dried over MgSO$_4$, filtered and concentrated. The crude material was separated into two lots (E-5A and E-5Ab) by column chromatography on silica gel using 10-30% acetone in dichloromethane. E-5A was obtained as a white foam (150 mg, 28%).

E-5Ab was obtained as a colourless oil (202 mg, 0.14 mmol 36%), which was subsequently dissolved in MeOH (1 mL) and cooled to 0° C. To this solution was added 1 drop of HCl/MeOH solution (1.25M) and stirred at 0° C. for 20 min. The solution was neutralized with the addition of solid NaHCO$_3$ and the MeOH was removed under reduced pressure. This residue was purified by column chromatography on silica gel using 10-30% acetone in dichloromethane to afford a second lot of E-5A (133 mg, 25%) as a white foam. Combined yield of E-5A for this process=285 mg, 54%.

Example 29

Preparation of Compound of Formula E-6A

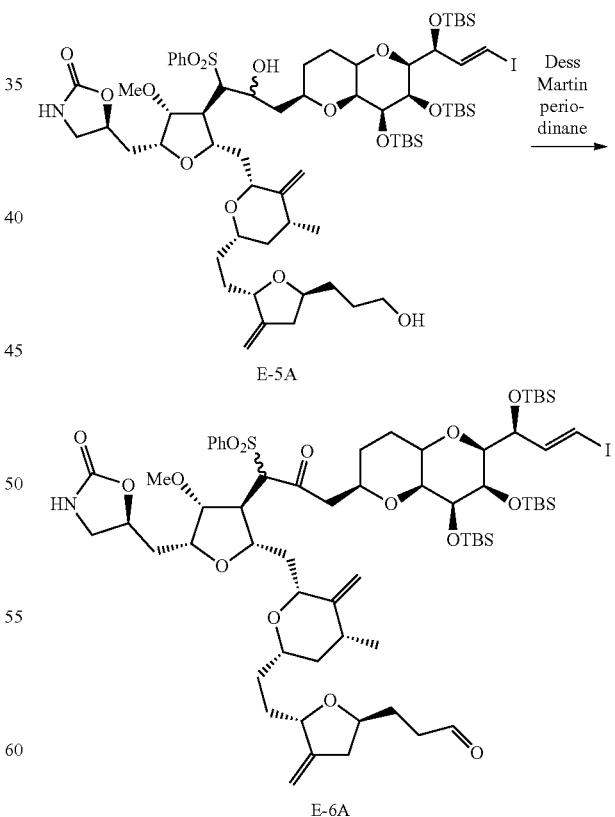

Compound E-5A (285 mg, 0.21 mmol, 1.0 eq.) was dissolved in dichloromethane (2 mL) at room temperature. Dess Martin periodinane (217 mg, 0.51 mmol, 2.5 eq) was added in one portion and the reaction mixture was stirred for 1.5 hours. The reaction was quenched by the addition of saturated aqueous sodium bicarbonate solution (4 mL) and 10% (w/w) sodium thiosulfate solution (4 mL) and further diluted with MTBE (5 mL). The resulting mixture was stirred for 30 min, diluted with brine (4 mL) and the layers were separated. The aqueous phase was further extracted with MTBE (2×5 mL) and the combined organic layers were washed with brine (10 mL), dried over MgSO$_4$, filtered and concentrated. The crude product was purified by column chromatography on silica gel using 5-20% acetone in dichloromethane as an eluent. The product E-6A was afforded as a colourless oil (174 mg, 61%).

Example 30

Preparation of compound of formula E-8A

All reagents are stored in a glovebox. A 50 mL round-bottom flask equipped with a stir bar was oven dried and cooled under inert atmosphere during introduction to the glovebox. To a 50 mL round-bottom flask equipped with a stir bar, under inert atmosphere, were added CrCl$_3$·3THF (47 mg, 0.13 mmol, 1.0 eq), 4,4'-tert-butyl-2,2'-bipyridyl (34 mg, 0.13 mmol, 1.0 eq), NiCl$_2$·dmp (8 mg, 0.03 mmol, 0.2 eq), manganese (28 mg, 0.50 mmol, 4.0 eq) and Zr(Cp)$_2$Cl$_2$ (55 mg, 0.19 mmol, 1.5 eq). The reaction vessel was sealed with a rubber septum and brought outside the glovebox. Anhydrous THF (5 mL) was added to the round bottom flask and the resulting mixture was stirred at room temperature for 30 minutes.

Compound E-6A (174 mg, 0.13 mmol, 1.0 eq.) was dissolved in anhydrous THF (5 mL) and added to the reaction mixture dropwise at room temperature and allowed to stir for 16 hours. The reaction mixture was then poured into a slurry of florisil (5 g) in MTBE (50 mL) and stirred

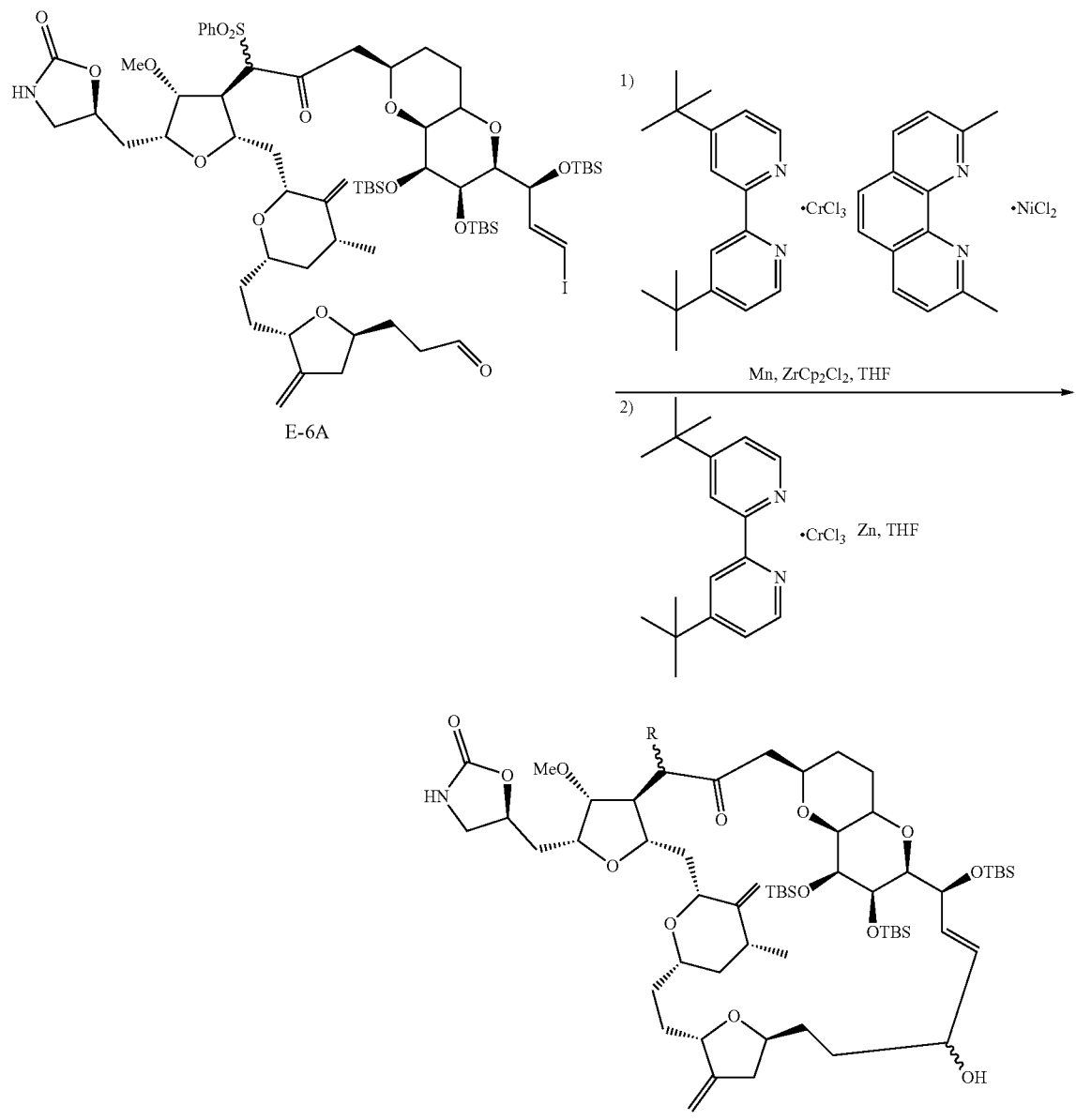

E-7A, R = SO$_2$PH
E-8A, R = H for 30 minutes. The mixture was filtered over celite and concentrated to afford a mixture of the products E-7A/E-8A (-1:3) as a colourless oil (80 mg).

A 50 mL round-bottom flask was charged with E-7A/E-8A mixture (110 mg, 87 μmol, 1.0 eq), equipped with a stir bar and introduced into a glovebox. To the reaction vessel were added CrCl$_3$·3THF (196 mg, 0.52 mmol, 6.0 eq), 4,4'-tert-butyl-2,2'-bipyridyl (211 mg, 0.79 mmol, 9.0 eq) and Zn (173 mg, 2.6 mmol, 30.0 eq). The round-bottom flask was sealed with a rubber septum and brought outside the glovebox. Anhydrous THF (10 mL) was added to the reaction mixture and stirred at room temperature for 16 hours. The solvent was then removed under reduced pressure. The residue was suspended in dichloromethane and filtered over celite to remove Zn metal. The filtrate was applied to silica gel and the product alcohol E-8A (56 mg, 58%) was isolated by column chromatography, using 10-30% acetone in dichloromethane as an eluent.

Example 31

Preparation of Compound of Formula E-9A

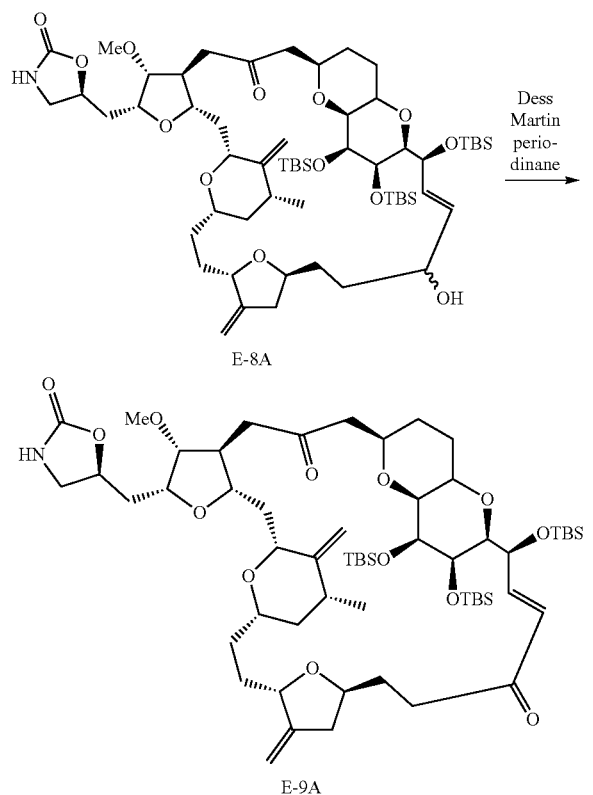

Example 32

Preparation of Compound of Formula E-10A

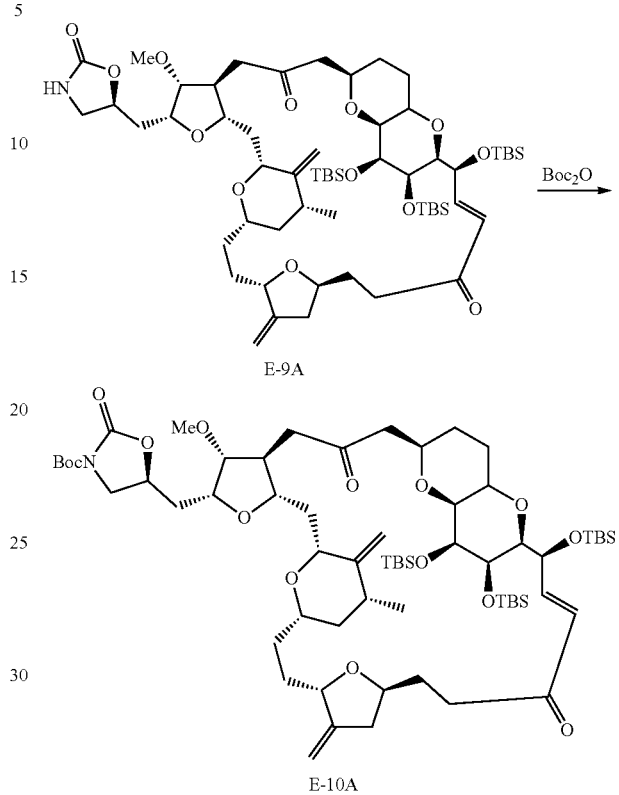

Compound E-9A (51 mg, 46 μmol, 1.0 eq.) was dissolved in anhydrous THF (1 mL) at room temperature. To this solution was added triethylamine (10 μL, 69 μmol, 1.5 eq.), DMAP (8 mg, 69 μmol, 1.5 eq.) and an excess of di-tert-butyl dicarbonate (>50 mg, 228 μmol, 5.0 eq). The reaction mixture was stirred for 1 hour. The reaction solvent was removed under reduced pressure, the residue was redissolved in dichloromethane and applied to silica gel for column chromatography using 5-10% acetone in dichloromethane. The product E-10A was afforded as an amorphous white solid (50 mg, 89%).

Example 33

Preparation of Compound of Formula E-10C

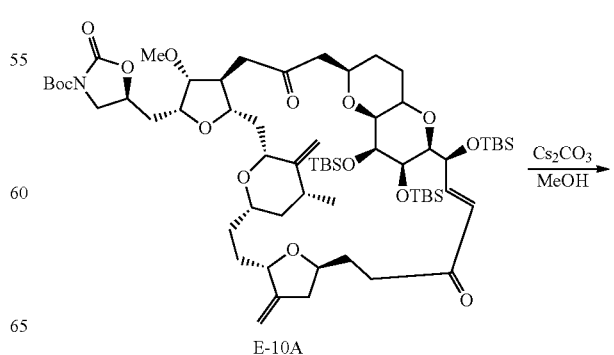

Compound E-8A (56 mg, 50 μmol, 1.0 eq.) was dissolved in dichloromethane (1 mL) at room temperature. Dess Martin periodinane (23 mg, 55 μmol, 1.1 eq) was added in one portion and the reaction mixture was stirred for 1.5 hours. The reaction mixture was loaded directly on silica gel for column chromatography using 5-20% acetone in dichloromethane as an eluent. Product E-9A was afforded as a colourless oil (51 mg, 91%).

-continued

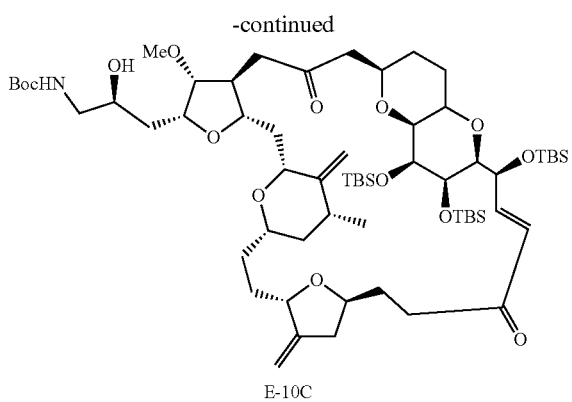

E-10C

Compound E-10A (50 mg, 41 μmol, 1.0 eq) was dissolved in MeOH (1 mL). Cesium carbonate (9 mg, 29 μmol, 0.70 eq) was added in one portion at room temperature and the reaction was stirred at room temperature for 16 hours. The solvent was removed under reduced pressure. The residue was redissolved in dichloromethane and applied to silica gel for column chromatography using 10-20% acetone in dichloromethane. The product E-10C was afforded as a colourless oil (43 mg, 88%).

Example 34

Preparation of Compound 5q

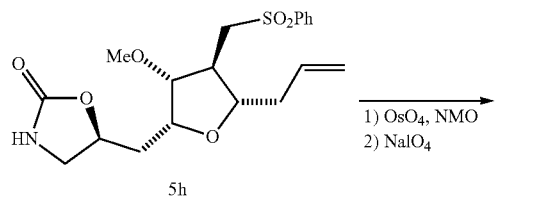
5h $\xrightarrow{\text{1) OsO}_4, \text{NMO} \quad \text{2) NaIO}_4}$

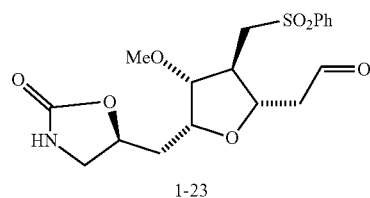
1-23

Compound 1-23 is prepared in a manner analogous to that described in Example 12.

EMBODIMENTS

1. The compound of formula 1, or a pharmaceutically acceptable salt thereof:

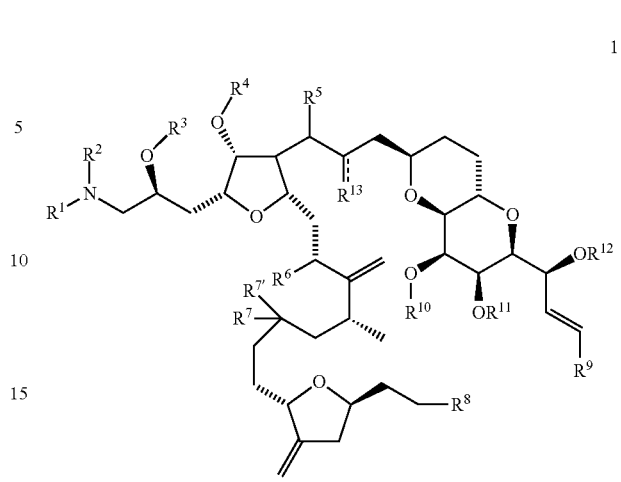

wherein $R^1$ and $R^2$ each independently is H, a silyl group, an acyl group, a sulfonyl group or an alkoxycarbonyl group; and $R^3$ is H or an alcohol protecting group;

or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms; and the remaining of $R^1$ and $R^2$ is H, a silyl group, an acyl group, a sulfonyl group or an alkoxycarbonyl group;

or one of $R^1$ and $R^2$ is absent and the other $R^1$ or $R^2$ together with the nitrogen atom to which it is attached form an azide, and $R^3$ is H or an alcohol protecting group;

$R^4$ is H, $C_{1-3}$ alkyl or $C_{1-3}$ haloalkyl or an alcohol protecting group;

$R^5$ is H or —SO$_2$Ar, wherein Ar is an aryl group;

$R^6$ is OR$^{16}$, wherein $R^{16}$ is H or an alcohol protecting group;

$R^7$ and $R^{7'}$ together form a =O or a protected geminal diol, or one of $R^7$ and $R^{7'}$ is H and the other is a leaving group or a functional group that can be converted into a leaving group;

or $R^6$ and one of $R^7$ and $R^{7'}$ together form —O—, and the other $R^7$ or $R^{7'}$ is H;

$R^8$ is —C(=O)R$^{17}$ or —CH$_2$OR$^{18}$; wherein $R^{17}$ is H or OR$^{19}$, wherein $R^{19}$ is H or a hydrocarbon, the hydrocarbon optionally having one or more heteroatoms;

$R^{18}$ is H or an alcohol protecting group;

$R^9$ is a halide or a sulfonate;

or $R^8$ and $R^9$ together form —C(=O)— or —CH(OR$^{20}$)—; wherein $R^{20}$ is H or an alcohol protecting group;

$R^{10}$, $R^{11}$ and $R^{12}$ each independently is H or an alcohol protecting group;

----- is a single or double bond; and $R^{13}$ is =O or —OR$^{21}$, wherein $R^{21}$ is H or an alcohol protecting group.

2. The compound according to embodiment 1, or a pharmaceutically acceptable salt thereof, wherein the compound has the structure of formula 1a:

3. The compound according to embodiment 1 or 2, wherein $R^{10}$, $R^{11}$ or $R^{12}$ is an alcohol protecting group.

4. The compound according to embodiment 1 or 2, wherein $R^{10}$, $R^{11}$ or $R^{12}$ is a silyl protecting group.

5. The compound according embodiment 3, wherein $R^{10}$, $R^{11}$ or $R^{12}$ is tert-butyldimethyl silyl (TBS).

6. The compound according to any one of embodiments 1 to 5, wherein $R^{13}$ is =O.

7. The compound according to any one of embodiments 1 to 6, wherein $R^9$ is I.

8. The compound according to any one of embodiments 1 to 7, wherein $R^8$ is —C(=O)H.

9. The compound according to any one of embodiments 1 to 6, wherein $R^8$ and $R^9$ together form —C(=O)—.

10. The compound of formula 2, or a pharmaceutically acceptable salt thereof:

wherein
$R^1$ and $R^2$ each independently is H, a silyl group, an acyl group, a sulfonyl group or an alkoxycarbonyl group; and $R^3$ is H or an alcohol protecting group;
or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms; and the remaining of $R^1$ and $R^2$ is H, a silyl group, an acyl group, a sulfonyl group or an alkoxycarbonyl group;
or one of $R^1$ and $R^2$ is absent and the other $R^1$ or $R^2$ together with the nitrogen atom to which it is attached form an azide, and $R^3$ is H or an alcohol protecting group;

$R^4$ is H, $C_{1-3}$ alkyl or $C_{1-3}$ haloalkyl or an alcohol protecting group;
one of $R^{5'}$ and $R^{5''}$ is H and other is —CH$_2$O$R^{28}$ or —CH$_2$SO$_2$—Ar, or $R^{5'}$ and $R^{5''}$ taken together form =CH—SO$_2$—Ar, wherein
$R^{28}$ is H or an alcohol protecting group; and
Ar is an aryl group;
$R^6$ is O$R^{16}$, wherein $R^{16}$ is H or an alcohol protecting group;
$R^7$ and $R^{7'}$ together form a =O or a protected geminal diol, or one of $R^7$ and $R^{7'}$ is H and the other is a leaving group or a functional group that can be converted into a leaving group;
or $R^6$ and one of $R^7$ and $R^{7'}$ together form —O—, and the other $R^7$ or $R^{7'}$ is H;
$R^8$ is —C(=O)$R^{17}$ or —CH$_2$O$R^{18}$; wherein
$R^{17}$ is H or O$R^{19}$, wherein $R^{19}$ is H or a hydrocarbon, the hydrocarbon optionally having one or more heteroatoms;
$R^{18}$ is H or an alcohol protecting group.

11. The compound according to embodiment 10, or a pharmaceutically acceptable salt thereof, wherein the compound has the structure of formula 2a:

12. The compound according to any one of embodiments 1, 2, 3, 4, 5, 6, 7, 10 and 11, wherein $R^8$ is —CH$_2$O$R^{18}$, wherein $R^{18}$ is H or an alcohol protecting group.

13. The compound according to embodiment 12, wherein $R^{18}$ is tert-butyldiphenyl silyl (TBDPS).

14. The compound of formula 5, or a salt thereof:

wherein,
$R^1$ and $R^2$ each independently is H, a silyl group, an acyl group, a sulfonyl group or an alkoxycarbonyl group; and $R^3$ is H or an alcohol protecting group;
or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms; and the remaining of $R^1$ and $R^2$ is H, a silyl group, an acyl group, a sulfonyl group or an alkoxycarbonyl group;

or one of $R^1$ and $R^2$ is absent and the other $R^1$ or $R^2$ together with the nitrogen atom to which it is attached form an azide, and $R^3$ is H or an alcohol protecting group;

$R^4$ is H, $C_{1-3}$ alkyl, $C_{1-3}$ haloalkyl or an alcohol protecting group;

one of $R^{5'}$ and $R^{5'''}$ is H and the other is —$CH_2OR^{28}$ or —$CH_2SO_2$—Ar, or $R^{5'}$ and $R^{5'''}$ taken together form =O or =CH—$SO_2$—Ar, wherein $R^{28}$ is H or an alcohol protecting group; and Ar is an aryl group; and $R^{6'}$ is —$CH_2$—CH=$CR^{29}R^{29'}$, —$CH_2C(=O)$—$R^{25}$ or —$CH_2$—$CH_2$—O—$R^{26}$, wherein $R^{29}$ and $R^{29'}$ each independently is H or a hydrocarbon, the hydrocarbon optionally having one or more heteroatoms;

$R^{25}$ is H or $OR^{27}$, wherein $R^{27}$ is H or a hydrocarbon, the hydrocarbon optionally having one or more heteroatoms;

$R^{26}$ is H or an alcohol protecting group; or $R^{6'}$ and one of $R^{5'}$ and $R^{5'''}$ together form a protected vicinal diol.

15. The compound according to embodiment 14, or a salt thereof, wherein the compound has the structure of formula 5a:

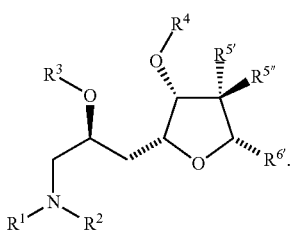

5a

16. The compound according to embodiment 14 or 15, wherein $R^{5'}$ is H and $R^{5'''}$ is —$CH_2SO_2$—Ar, wherein Ar is an aryl group.

17. The compound according to any one of embodiments 14 to 16, wherein $R^{6'}$ is —$CH_2C(=O)$—$R^{25}$, and wherein $R^{25}$ is H or $OR^{27}$, wherein $R^{27}$ is H or a hydrocarbon, the hydrocarbon optionally having one or more heteroatoms.

18. The compound according to any one of embodiments 1 to 17, wherein $R^3$ is H, a silyl group, an acyl group or an alkoxycarbonyl group.

19. The compound according to any one of embodiments 1 to 18, wherein $R^1$ and $R^2$ each independently is H, a silyl group, an acyl group, a sulfonyl group or an alkoxycarbonyl group, and at least one of $R^1$ and $R^2$ is other than H.

20. The compound according to any one of embodiments 1 to 17, wherein $R^3$ and one of $R^1$ and $R^2$ together form —C(=O)—, and other $R^1$ or $R^2$ is H, a silyl group, an acyl group or an alkoxycarbonyl group.

21. The compound according to any one of embodiments 1 to 20, wherein $R^4$ is $C_{1-3}$ alkyl group.

22. The compound according to any one of embodiments 1 to 20, wherein $R^4$ is benzyl.

23. A process for preparation of a compound of formula 3, or a pharmaceutically acceptable salt thereof, the process comprising

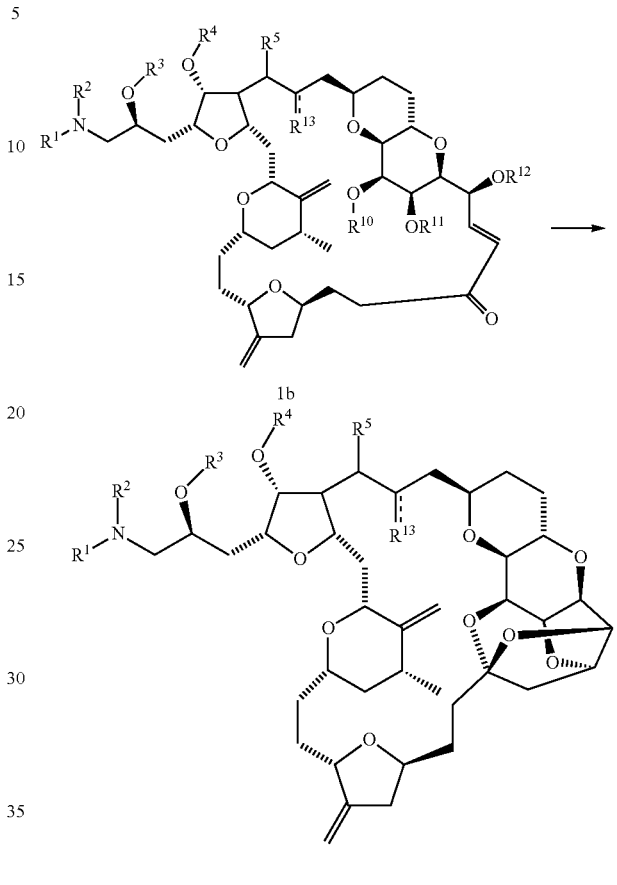

performing an intramolecular cyclization reaction on a compound of formula 1b to form the compound of formula 3, wherein $R^1$ and $R^2$ each independently is H, a silyl group, an acyl group, a sulfonyl group or an alkoxycarbonyl group; and $R^3$ is H or an alcohol protecting group;

or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms; and the remaining of $R^1$ and $R^2$ is H, a silyl group, an acyl group, a sulfonyl group or an alkoxycarbonyl group;

or one of $R^1$ and $R^2$ is absent and the other $R^1$ or $R^2$ together with the nitrogen atom to which it is attached form an azide, and $R^3$ is H or an alcohol protecting group;

$R^4$ is H, $C_{1-3}$ alkyl or $C_{1-3}$ haloalkyl or an alcohol protecting group;

$R^5$ is H or —$SO_2$Ar, wherein Ar is an aryl group;

$R^{10}$, $R^{11}$ and $R^{12}$ each independently is H or an alcohol protecting group;

----- is a single or double bond; and $R^{13}$ is =O or —$OR^{21}$, wherein $R^{21}$ is H or an alcohol protecting group.

24. A process for preparation of a compound of formula 1, or a pharmaceutically acceptable salt thereof, the process comprising:

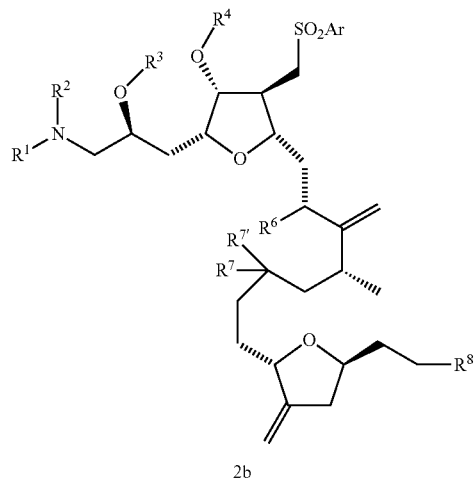

2b

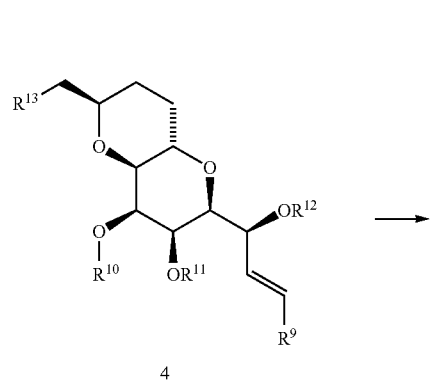

4

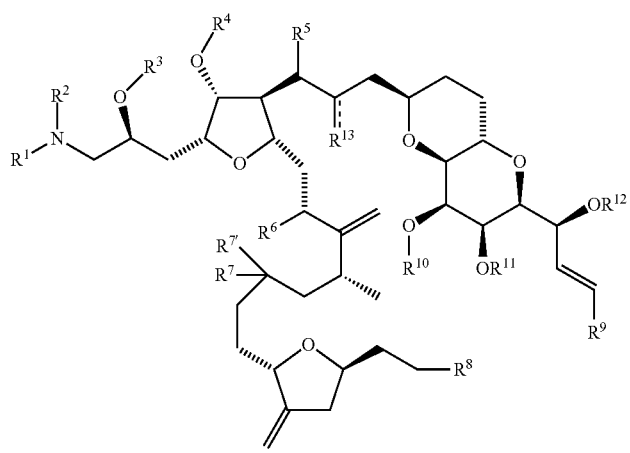

1 coupling a compound of formula 2b with a compound of formula 4 to form the compound of formula 1; wherein $R^1$ and $R^2$ each independently is H, a silyl group, an acyl group, a sulfonyl group or an alkoxycarbonyl group; and $R^3$ is H or an alcohol protecting group;

or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms; and the remaining of $R^1$ and $R^2$ is H, a silyl group, an acyl group, a sulfonyl group or an alkoxycarbonyl group;

or one of $R^1$ and $R^2$ is absent and the other $R^1$ or $R^2$ together with the nitrogen atom to which it is attached form an azide, and $R^3$ is H or an alcohol protecting group;

$R^4$ is H, $C_{1-3}$ alkyl or $C_{1-3}$ haloalkyl or an alcohol protecting group;

$R^5$ is H or —$SO_2Ar$, wherein Ar is an aryl group;

$R^6$ is $OR^{16}$, wherein $R^{16}$ is H or an alcohol protecting group;

$R^7$ and $R^{7'}$ together form a =O or a protected geminal diol, or one of $R^7$ and $R^{7'}$ is H and the other is a leaving group or a functional group that can be converted into a leaving group;

or $R^6$ and one of $R^7$ and $R^{7'}$ together form —O—, and the other $R^7$ or $R^{7'}$ is H;

$R^8$ is —C(=O)$R^{17}$ or —$CH_2OR^{18}$; wherein $R^{17}$ is H or $OR^{19}$, wherein $R^{19}$ is H or a hydrocarbon, the hydrocarbon optionally having one or more heteroatoms;

$R^{18}$ is H or an alcohol protecting group;

$R^9$ is a halide or a sulfonate;

or $R^8$ and $R^9$ together form —C(=O)— or —CH($OR^{20}$)—; wherein $R^{20}$ is H or an alcohol protecting group;

$R^{10}$, $R^{11}$ and $R^{12}$ each independently is H or an alcohol protecting group;

- - - - - is a single or a double bond;

$R^{13}$ is =O or —$OR^{21}$, wherein $R^{21}$ is H or an alcohol protecting group; and $R^{13'}$ is —C(=O)$R^{22}$, wherein $R^{22}$ is H or $OR^{23}$, wherein $R^{23}$ is H or a hydrocarbon, the hydrocarbon optionally having one or more heteroatoms.

25. The process according to embodiment 24, wherein the coupling reaction is performed using a base.

26. The process according to embodiment 25, wherein the base is n-butyllithium.

27. A process for preparation of compound of formula 2, or a pharmaceutically acceptable salt thereof, the process comprising:

63

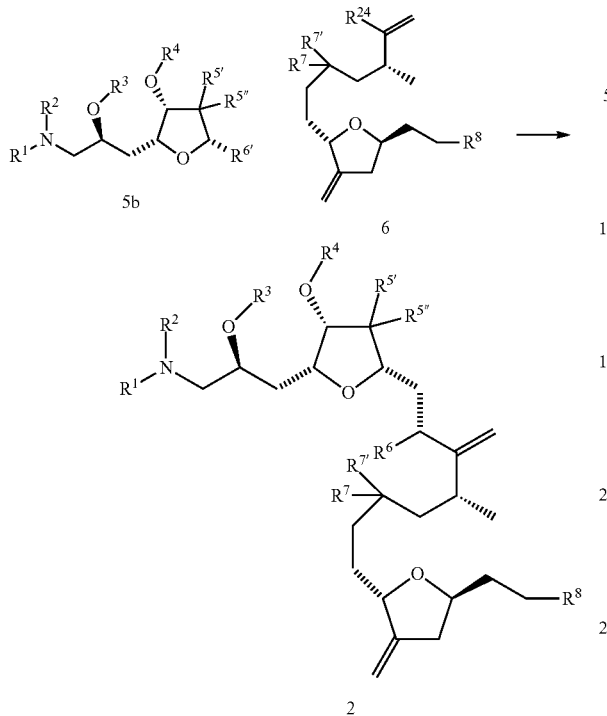

5b

6

2 coupling a compound of formula 5b with a compound of formula 6, wherein
- $R^1$ and $R^2$ each independently is H, a silyl group, an acyl group, a sulfonyl group or an alkoxycarbonyl group; and $R^3$ is H or an alcohol protecting group;
- or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms; and the remaining of $R^1$ and $R^2$ is H, a silyl group, an acyl group, a sulfonyl group or an alkoxycarbonyl group;
- or one of $R^1$ and $R^2$ is absent and the other $R^1$ or $R^2$ together with the nitrogen atom to which it is attached form an azide, and $R^3$ is H or an alcohol protecting group;
- $R^4$ is H, $C_{1-3}$ alkyl or $C_{1-3}$ haloalkyl or an alcohol protecting group;
- one of $R^{5'}$ and $R^{5''}$ is H and the other is —$CH_2OR^{28}$ or —$CH_2SO_2$—Ar, or $R^{5'}$ and $R^{5''}$ taken together form =CH—$SO_2$—Ar, wherein
  - $R^{28}$ is H or an alcohol protecting group; and
  - Ar is an aryl group;
- $R^6$ is $OR^{16}$, wherein $R^{16}$ is H or an alcohol protecting group;
- $R^7$ and $R^{7'}$ together form a =O or a protected geminal diol, or one of $R^7$ and $R^{7'}$ is H and the other is a leaving group or a functional group that can be converted into a leaving group;
- or $R^6$ and one of $R^7$ and $R^{7'}$ together form —O—, and the other $R^7$ or $R^{7'}$ is H;
- $R^{6'}$ is —$CH_2C(=O)R^{25}$ or —$CH_2CH_2OR^{26}$; wherein
  - $R^{25}$ is H or $OR^{27}$, wherein $R^{27}$ is H or a hydrocarbon, the hydrocarbon optionally having one or more heteroatoms;
  - $R^{26}$ is H or an alcohol protecting group;

64

- $R^8$ is —C(=O)$R^{17}$ or —$CH_2OR^{18}$; wherein
  - $R^{17}$ is H or $OR^{19}$, wherein $R^{19}$ is H or a hydrocarbon, the hydrocarbon optionally having one or more heteroatoms;
  - $R^{18}$ is H or an alcohol protecting group; and
- $R^{24}$ is a halide or a sulfonate.

28. The process according to embodiment 27, wherein $R^{6'}$ is —$CH_2C(=O)H$, and the coupling reaction is performed using a nickel/chromium catalyst.

29. A process for preparation of the compound of formula 5, or a salt thereof, the process comprising:
converting the terminal alcohol of the compound of formula 7 into an amine or substituted amine to form the compound of formula 5

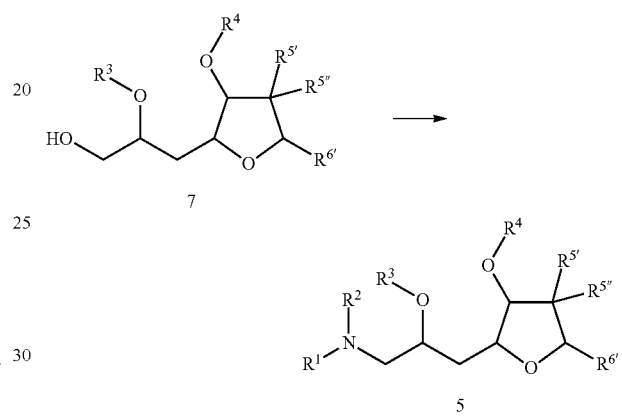

7

5 wherein
- $R^1$ and $R^2$ each independently is H, a silyl group, an acyl group, a sulfonyl group or an alkoxycarbonyl group; and $R^3$ is H or an alcohol protecting group;
- or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms; and the remaining of $R^1$ and $R^2$ is H, a silyl group, an acyl group, a sulfonyl group or an alkoxycarbonyl group;
- or one of $R^1$ and $R^2$ is absent and the other $R^1$ or $R^2$ together with the nitrogen atom to which it is attached form an azide, and $R^3$ is H or an alcohol protecting group;
- $R^4$ is H, $C_{1-3}$ alkyl or $C_{i-3}$ haloalkyl or an alcohol protecting group;
- one of $R^{5'}$ and $R^{5''}$ is H and the other is —$CH_2OR^{28}$ or —$CH_2SO_2$—Ar, or $R^{5'}$ and $R^{5''}$ taken together form =O or =CH—$SO_2$—Ar, wherein
  - $R^{28}$ is H or an alcohol protecting group; and
  - Ar is an aryl group; and
- $R^{6'}$ is —$CH_2$—CH=$CR^{29}R^{29'}$, —$CH_2C(=O)$—$R^{25}$ or —$CH_2$—$CH_2$—O—$R^{26}$, wherein
  - $R^{29}$ and $R^{29'}$ each independently is H or a hydrocarbon, the hydrocarbon optionally having one or more heteroatoms;
  - $R^{25}$ is H or $OR^{27}$, wherein $R^{27}$ is H or a hydrocarbon, the hydrocarbon optionally having one or more heteroatoms; and
  - $R^{26}$ is H or an alcohol protecting group.

30. A process for preparation of Eribulin, comprising the process as defined in any one of embodiments 23 to 29.

31. A process for preparation an analog of halichondrin, comprising the process as defined in any one of embodiments 23 to 29.

32. Eribulin mesylate having a purity of more than 95%, 96%, 97%, 98% or 99%, as determined by HPLC.

33. N-(tert-butoxycarbonyl) Eribulin

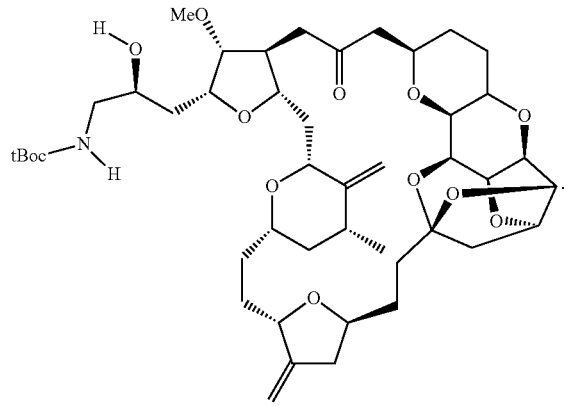

34. A compound of formula 3a

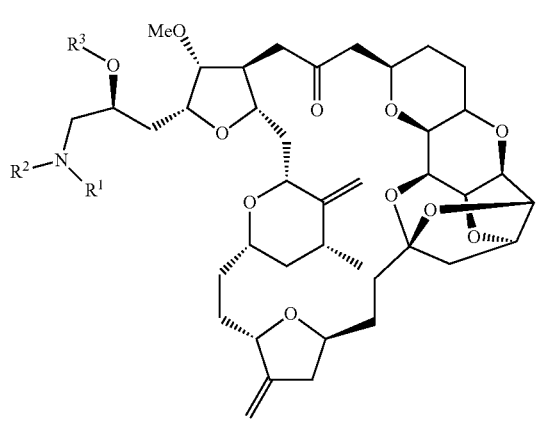

wherein,

R$^1$ is an acyl group, a sulfonyl group or an alkoxycarbonyl group;

R$^2$ and R$^3$ are both H or together form —C(=O)—, —C(=O)—C(=O)— or —C(R$^{14}$)(R$^{15}$)—, wherein R$^{14}$ and R$^{15}$ each independently is H or a hydrocarbon, the hydrocarbon optionally having one or more heteroatoms.

35. The compound of embodiment 34, wherein R$^1$ is tert-butoxycarbonyl, and R$^2$ and R$^3$ together form —C(=O)—.

36. The compound of embodiment 34, wherein R$^1$ is tert-butoxycarbonyl, and R$^2$ and R$^3$ together form —C(Me)$_2$.

Certain adaptations and modifications of the described embodiments can be made. Therefore, the above discussed embodiments are considered to be illustrative and not restrictive.

What is claimed is:

1. A process for preparation of a compound of formula 3, or a pharmaceutically acceptable salt thereof, the process comprising:

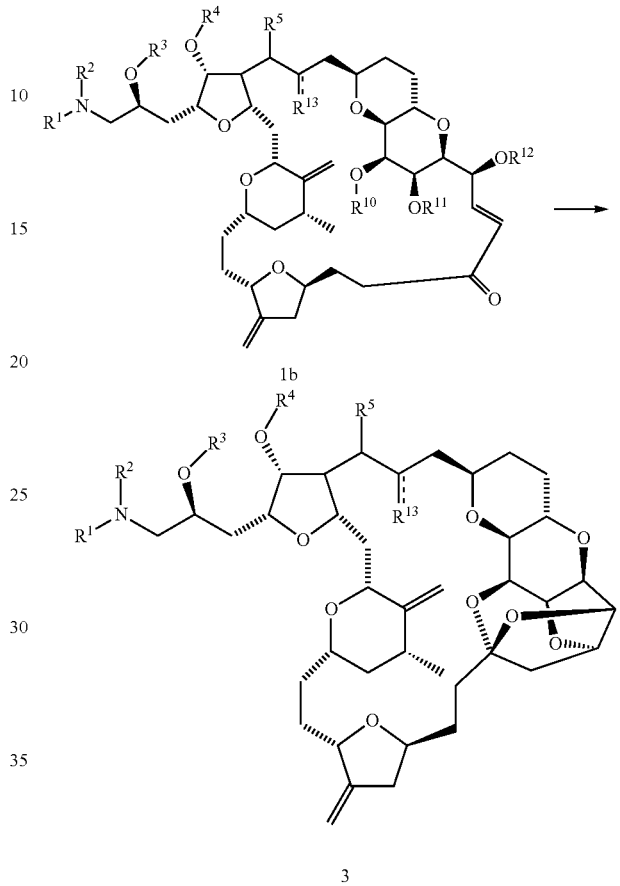

performing an intramolecular cyclization reaction using an acid selected from the group consisting of pyridinium p-toluenesulfonate, trialkyl ammonium sulfate and acetic acid, on a compound of formula 1b to form the compound of formula 3, wherein R$^1$ and R$^2$ each independently is H, a silyl protecting group, an acyl group having the formula RC(=O)— where each R is a hydrocarbon individually selected from methyl, ethoxyethyl, 2-pyridyl and trifluoromethyl, a sulfonyl group having the formula RSO$_2$— where each R is a hydrocarbon individually selected from methyl, ethoxyethyl, 2-pyridyl and trifluoromethyl or an alkoxycarbonyl group, wherein said alkoxycarbonyl group is an amine protecting group; or one of R$^1$ and R$^2$ is absent and the other R$^1$ or R$^2$ together with the nitrogen atom to which it is attached form an azide;

R$^3$ is H or an alcohol protecting group;

or R$^3$ and one of R$^1$ and R$^2$ together form —C(=O)—, —C(=O)—C(=O)—or —C(R$^{14}$)(R$^{15}$)—, wherein R$^{14}$ and R$^{15}$ each independently is H or a hydrocarbon selected from methyl, ethoxyethyl, 2-pyridyl and trifluoromethyl, R$^4$ is H, C$_{1-3}$ alkyl or C$_{1-3}$ haloalkyl or an alcohol protecting group;

R$^5$ is H or SO$_2$Ar, wherein Ar is a C$_6$ through C$_{14}$ aryl protecting group;

$R^{10}$, $R^{11}$ and $R^{12}$ each independently is H or an alcohol protecting group;

- - - - - is a single or double bond; and $R^{13}$ is =O or —$OR^{21}$, wherein $R^{21}$ is H or an alcohol protecting group; and treating said reaction product with a base selected from the group consisting of alkali metal carbonates and alkali metal phosphates.

2. The process of claim 1, wherein the compound of formula 3 is Eribulin.

3. N-(tert-butoxycarbonyl) eribulin

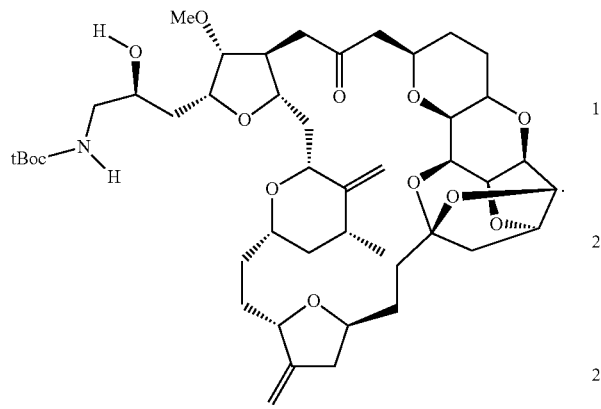

4. A compound of formula 3a

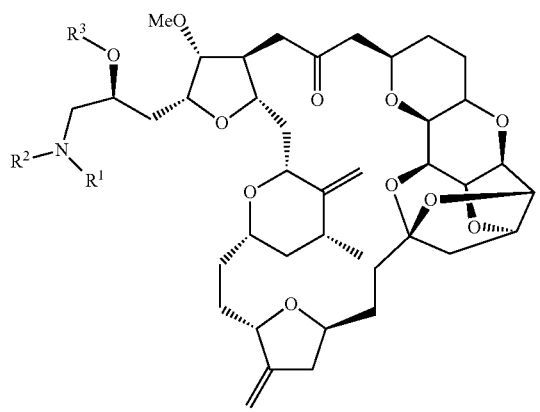

wherein, $R^1$ is tert-butoxycarbonyl;

$R^2$ and $R^3$ together form —C(=O)— or —C(Me)$_2$—.

* * * * *